(12) United States Patent
Jacobson et al.

(10) Patent No.: US 9,227,979 B2
(45) Date of Patent: Jan. 5, 2016

(54) FLUORESCENT ANTAGONISTS OF THE A3 ADENOSINE RECEPTOR

(71) Applicants: The United States of America, as represented by the Secretary, Department of Health and Human Services, Bethesda, MD (US); Universita Degli Studi Di Trieste, Trieste (IT); Universita Degli Studi Di Padova, Padua (IT)

(72) Inventors: Kenneth A. Jacobson, Silver Spring, MD (US); Santhosh Kumar Thatikonda, Woburn, MA (US); Eszter Erika Kozma, Washington, DC (US); Giampiero Spalluto, Ferrara (IT); Stefano Moro, Padua (IT); Stephanie Federico, Trieste (IT)

(73) Assignees: The United States of America, as represented by The Secretary, Department of Health and Human Services, Washington, DC (US); Universita Degli Studi Di Trieste, Trieste (IT); Universita Degli Studi Di Padova, Padua (IT)

( * ) Notice: Subject to any disclaimer, the term of this patent is extended or adjusted under 35 U.S.C. 154(b) by 1 day.

(21) Appl. No.: 13/748,826

(22) Filed: Jan. 24, 2013

(65) Prior Publication Data
US 2013/0190335 A1 Jul. 25, 2013

Related U.S. Application Data

(60) Provisional application No. 61/590,596, filed on Jan. 25, 2012.

(51) Int. Cl.
*C07D 487/14* (2006.01)
*C07D 487/04* (2006.01)

(52) U.S. Cl.
CPC ............ *C07D 487/14* (2013.01); *C07D 487/04* (2013.01)

(58) Field of Classification Search
USPC .......... 514/256, 257, 267, 272, 383; 544/249, 544/251, 252; 548/262.2, 262.4, 266.2
See application file for complete search history.

(56) References Cited

U.S. PATENT DOCUMENTS 6,066,642 A * 5/2000 Jacobson et al. ............. 514/267
6,407,236 B1 * 6/2002 Baraldi et al. ................ 544/251
6,528,516 B1 3/2003 Civan et al.
6,921,825 B2 * 7/2005 Baraldi et al. ................ 544/251

FOREIGN PATENT DOCUMENTS

WO WO 0395457 A1 * 11/2003
WO WO 2008/055711 A2 5/2008

OTHER PUBLICATIONS

Muller et al., Current Topics in Medicinal Chemistry vol. 3, pp. 445-462. Published 2003.*
Tosh et al., Bioorganic and Medicinal Chemistry vol. 18, pp. 508-517. Published 2010.*
Tosh, D.K. et al., Bioorganic and Medicinal Chemistry vol. 18, pp. 508-517 published 2010.*
"Alexa Fluor," downloaded from Wikipedia on Jul. 17, 2013, http://en.wikipedia.org/wiki/Alexa_Fluor.
"The Alexa Fluor Dye Series—Note 1.1," downloaded Jul. 17, 2013, http://www.invitrogen.com/site/us/en/home/References/Molecular-Probes-The-Handbook/Technical-Notes-and-Product-Highlights/The-Alexa-Fluor-Dye-Series.html.
"Alexa Fluor Dyes Spanning the Visible and Infrared Spectrum—Section 1.3," downloaded on Jul. 17, 2013, http://www.invitrogen.com/site/us/en/home/References/Molecular-Probes-The-Handbook/Fluorophores-and-Their-Amine-Reactive-Derivatives/Alexa-Fluor-Dyes-Spanning-the-Visible-and-Infrared-Spectrum.html.
"Fluorescence quantum yields (QY) and lifetimes (τ) for Alexa Fluor dyes—Table 1.5," downloaded Jul. 17, 2013, http://www.invitrogen.com/site/use/en/home/References/Molecular-Probes-The-Handbook/tables/Fluorescence-quantum-yields-and-lifetimes-for-Alexa-Fluor-dyes.html.
Bajaj, A, et al., "A fluorescent alpha-factor analogue exhibits multiple steps on binding to its G protein coupled receptor in yeast," *Biochemistry*, vol. 43, No. 42, pp. 13564-13578 (Oct. 26, 2004) (Abstract).
Ballard, JL, et al., "Comparison of Alexa Fluor and CyDye for practical DNA microarray use," *Molecular Biotechnology*, vol. 36, No. 3, pp. 175-183 (Jul. 2007) (Abstract).
Baraldi, P G, et al., "Pyrazolo[4,3-e]-1,2,4-triazolo[1,5-c]pyrimidine derivatives as highly potent and selective human A(3) adenosine receptor antagonists," *Journal of Medicinal Chemistry*, vol. 42, No. 22, pp. 4473-4478 (1999) (Abstract).
Berlier, Judith E., et al., "Quantitative Comparison of Long-wavelength Alexa Fluor Dyes to Cy Dyes: Fluorescence of the Dyes and Their Bioconjugates," *The Journal of Histochemistry & Cytochemistry*, vol. 51, No. 12, pp. 1699-1712 (2003).

(Continued)

Primary Examiner — Wu-Cheng Winston Shen
Assistant Examiner — George W Kosturko
(74) Attorney, Agent, or Firm — Leydig, Voit & Mayer

(57) ABSTRACT

Disclosed are compounds of the formula (I) which are fluorescently labeled antagonists of the $A_3$ adenosine receptor:

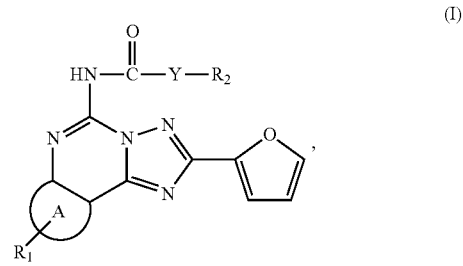

(I)

wherein A, $R_1$, $R_2$, and Y are as described herein. Also disclosed are diagnostic compositions and a method of diagnosis of a patient for a possible treatment by an antagonist of the $A_3$ adenosine receptor, involving the use of one or more of these compounds as diagnostic agents.

13 Claims, 15 Drawing Sheets

(56) References Cited

OTHER PUBLICATIONS

Bradford, Marion M., "A Rapid and Sensitive Method for the Quantitation of Microgram Quantities of Protein Utilizing the Principle of Protein-Dye Binding," *Analytical Biochemistry*, vol. 72, pp. 248-254 (1976).

Cohen, S., et al., "CF102 an $A_3$ Adenosine Receptor Agonist Mediates Anti-Tumor and Anti-Inflammatory Effects in the Liver," *Journal of Cellular Physiology*, vol. 226, pp. 2438-2447 (2011).

Cordeaux, Y., et al., "Agonist-occupied $A_3$ adenosine receptors exist within heterogeneous complexes in membrane microdomains of individual living cells," *The FASEB Journal*, vol. 22, pp. 850-860 (Mar. 2008).

Corriden, Ross, et al., "Using the fluorescent antagonist, XAC-X-BY630 to quantify antagonist-adenosine $A_3$ receptor complexes in membrane microdomains of single living cells," *Proceedings of the British Pharmacological Society*, vol. 7, No. 4 (2009) http://www.pA2online.org/abstracts/Vol7Issue4abst085P.pdf (Abstract).

Fishman, Pnina, et al., "Pharmacological and therapeutic effects of $A_3$ adenosine receptor agonists," *Drug Discovery Today*, vol. 17, Nos. 7/8, pp. 359-366 (Apr. 2012).

Fredholm, Bertil B., et al., "International Union of Basic and Clinical Pharmacology. LXXXI. Nomenclature and Classification of Adenosine Receptors—An Update," *Pharmacological Reviews*, vol. 63, No. 1, pp. 1-63, (2011).

Garner, Amanda L., et al., "cat-ELCCA: A Robust Method to Monitor the Fatty Acid Acyltransferase Activity of Ghrelin O-Acyltransferase (GOAT)," *Angewandte Chemie International Edition England*, vol. 49, No. 50, pp. 9630-9634 (Dec. 10, 2010).

Gessi, Stefania, et al., "Elevated Expression of $A_3$ Adenosine Receptors in Human Colorectal Cancer Is Reflected in Peripheral Blood Cells," *Clinical Cancer Research*, vol. 10, pp. 5895-5901 (Sep. 1, 2004).

Gessi, S., et al., "Adenosine receptor targeting in health and disease," *Expert Opinion on Investigational Drugs*, vol. 20, No. 12, pp. 1591-1609 (Dec. 2011) (Abstract).

Ghai, G., et al., "Pharmacological characterization of CGS 15943A: a novel nonxanthine adenosine antagonist," *The Journal of Pharmacology and Experimental Therapeutics*, vol. 242, No. 3, pp. 784-790 (Sep. 1987) (Abstract).

Gao, Zhan-Guo, et al., "$N^6$-Substituted adenosine derivatives: selectivity, efficacy, and species differences at $A_3$ adenosine receptors," *Biochemical Pharmacology*, vol. 65, pp. 1675-1684 (2003).

Jaakola, Veli-Pekka, et al., "The 2.6 Angstrom Crystal Structure of a Human $A_{2A}$ Adenosine Receptor Bound to an Antagonist," *Science*, vol. 322, pp. 1211-1217 (Nov. 21, 2008).

Kecskés, Miklós, et al., "Novel Alexa Fluor-488 labeled antagonist of the $A_{2A}$ adenosine receptor: Application to a fluorescence polarization-based receptor binding assay," *Biochemical Pharmacology*, vol. 80, pp. 506-511 (2010).

Kim, Yong-Chul, et al., "Derivatives of the Triazoloquinazoline Adenosine Antagonist (CGS15943) Are Selective for the Human $A_3$ Receptor Subtype," *Journal of Medicinal Chemistry*, vol. 39, pp. 4142-4148 (1996).

Kuder, K, et al., "Fluorescent GPCR ligands as new tools in pharmacology," *Current Medicinal Chemistry*, vol. 15, No. 21, pp. 2132-2143 (2008) (Abstract).

Labute, Paul, "LowModeMD—Implicit Low-Mode Velocity Filtering Applied to Conformational Search of Macrocycles and Protein Loops," *Journal of Chemical Information and Modeling*, vol. 50, pp. 792-800 (2010).

Lenzi, O, et al., "2-Phenylpyrazolo[4,3-d]pyrimidin-7-one as a new scaffold to obtain potent and selective human A3 adenosine receptor antagonists: new insights into the receptor-antagonist recognition," *Journal of Medicinal Chemistry*, vol. 52, No. 23, pp. 7640-7652 (Dec. 10, 2009).

McCABE, R. Tyler, et al., "2-[2-[4-[2-[2-[1,3-Dihydro-1,1-bis(4-hydroxyphenyl)-3-oxo-5-isobenzofuranthioureidyl]ethylaminocarbonyl]ethyl]phenyl]ethylamino]-5'-*N*ethylcarboxamidoadenosine (FITC-APEC): A Fluorescent Ligand for $A_{2A}$-Adenosine Receptors," *Journal of Fluorescence*, vol. 2, No. 4, pp. 217-223 (1992).

Middleton, RJ, et al., "Fluorophore-tagged GPCR ligands," *Current Opinion in Chemical Biology*, vol. 9, No. 5, pp. 517-525 (Oct. 2005) (Abstract).

Moro, S., et al., "Combined target-based and ligand-based drug design approach as a tool to define a novel 3D-pharmacophore model of human A3 adenosine receptor antagonists: pyrazolo[4,3-e]1,2,4-triazolo[1,5-c]pyrimidine derivatives as a key study," *Journal of Medicinal Chemistry*, vol. 48, No. 1, pp. 152-162 (Jan. 13, 2005) (Abstract).

Moses, JE, et al., "The growing applications of click chemistry," *Chemical Society Reviews*, vol. 36, No. 8, pp. 1249-1262 (Aug. 2007) (Abstract).

Müller, Christa E., et al., "Recent developments in adenosine receptor ligands and their potential as novel drugs," *Biochimica et Biophysica Acta*, vol. 1808, pp. 1290-1308 (2011).

Nielsen, TT, et al., "Facile synthesis of beta-cyclodextrin-dextran polymers by "click" chemistry," *Biomacromolecules*, vol. 11, No. 7, pp. 1710-1715 (Jul. 12, 2010) (Abstract).

Ochaion, A., et al., "The anti-inflammatory target $A_3$ adenosine receptor is over-expressed in rheumatoid arthritis, psoriasis and Crohn's disease," *Cellular Immunology*, vol. 258, pp. 115-122 (2009).

Okamura, T., et al., "Structure-activity relationships of adenosine A3 receptor ligands: new potential therapy for the treatment of glaucoma," *Bioorganic & Medicinal Chemistry Letters*, vol. 14, No. 14, pp. 3775-3779 (Jul. 26, 2004) (Abstract).

Panchuk-Voloshina, Nataliya, et al., "Alexa Dyes, a Series of New Fluorescent Dyes that Yield Exceptionally Bright, Photostable Conjugates," *The Journal of Histochemistry & Cytochemistry*, vol. 47, No. 9, pp. 1179-1188 (1999).

Ramkumar, Vickram, et al., "The $A_3$ Adenosine Receptor Is the Unique Adenosine Receptor Which Facilitates Release of Allergic Mediators in Mast Cells," *The Journal of Biological Chemistry*, vol. 268, No. 23, pp. 16887-16890 (Aug. 15, 1993).

Simons, Peter C., et al., "Ligand-Receptor-G-Protein Molecular Assemblies on Beads for Mechanistic Studies and Screening by Flow Cytometry," *Molecular Pharmacology*, vol. 64, No. 5, pp. 1227-1238 (2003).

Wang, Zhao, et al., "Nucleoside-derived antagonists to $A_3$ adenosine receptors lower mouse intraocular pressure and act across species," *Experimental Eye Research*, vol. 90, pp. 146-154 (2010).

Weng, Kaizhi, et al., "Clinical reagents of GM-CSF and IFN-α induce the generation of functional chronic myeloid leukemia dendritic cells in vitro," *Cytotechnology*, vol. 64, pp. 75-81 (2012).

\* cited by examiner

X= (CH$_2$)$_3$, (CH$_2$)$_4$, (CH$_2$)$_5$, (CH$_2$CH$_2$O)$_2$CH$_2$CH$_2$, CH$_2$CH$_2$CH$_2$O(CH$_2$CH$_2$O)$_2$CH$_2$CH$_2$CH$_2$

X= (CH$_2$)$_2$, (CH$_2$)$_3$, (CH$_2$)$_4$, (CH$_2$)$_5$ $R_1$ = small alkyl ($C_1$ - $C_6$); m, n = 1 - 6 (preferred: m = 6, n = 3)

$R_2$ (fluorophore) = fluorescein other fluorescent dye that is compatible with biological systems Cy5 + other cyanine dyes AlexaFluor488 other AlexaFluor dyes

FLUORESCENT ANTAGONISTS OF THE A3 ADENOSINE RECEPTOR

CROSS-REFERENCE TO A RELATED APPLICATION

This patent application claims the benefit of U.S. Provisional Patent Application No. 61/590,596, filed Jan. 25, 2012, which is incorporated by reference.

BACKGROUND OF THE INVENTION

Activation of the Gi protein-coupled $A_3$ adenosine receptor (AR) is associated with anticancer, antiischemic and antiinflammatory effects, and clinical trials of several prototypical selective agonists are underway. See, for example, Ochaion, A., et al., *Cell Immunol.* 2009, 258:115-122; and Cohen, S., et al., *J. Cell. Physiol.* 2011, 226: 2438-2447. $A_3$AR antagonists are being examined as promising agents for the treatment of glaucoma. Wang, Z., et al., *Exp. Eye Res.* 2010, 90:146-154; and Okamura, T., et al., *Bioorg. Med. Chem. Lett.* 2004, 14: 3775-3779. Characterization of the $A_3$AR in tissues and assays to establish a structure-activity relationship (SAR) of newly synthesized compounds for drug discovery, as for many other G protein-coupled receptors (GPCRs), is often dependent on the use of high affinity radioligands. Fredholm, B. B., et al., *Pharmacol Rev* 2011; 63:1-34. Fluorescent agonists and antagonists of GPCRs have been studied as molecular probes for binding experiments. Middleton R. J., et al., *Curr Opin Chem Biol* 2005; 9:517-25; Kuder, K., et al., *Curr. Med. Chem.* 2008; 15:2132-43; Bajaj, A., et al., *Biochemistry* 2004; 43:13564-13578. Recently, several 4,4-difluoro-4-bora-3a,4a-diaza-s-indacene (BODIPY) derivatives have been reported as fluorescent ligands of the ARs, including the $A_3$AR. Cordeaux, Y., et al., *FASEB J* 2008; 22:850-60; Corriden, R., et al., *Proc. Brit. Pharmacol. Soc.*, 2009, vol. 7, Abstract 086P. http://www.pA2online.org/abstracts/Vol7Issue4abst086P.pdf, and used to study receptor complexes. However, many of these fluorescent tracers are relatively nonselective within the AR family.

Receptor-selective fluorescent ligands are used increasingly as tools for the study of receptor physiology and pathophysiology at the cellular and even the subcellular level; Kuder et al., infra. Furthermore, they are being increasingly investigated as tools in drug discovery research; Middleton, R. J., et al., infra. In both cases, techniques employing receptor-selective fluorescent ligands have proved to be complementary to, and in several cases even superior to, the traditional radioligand-based techniques. Increasing costs and public concerns associated with radioactive isotope handling and disposal are also making the use of fluorescent ligands more attractive in research and diagnostics. With the increasing importance of GPCRs in pharmacology and the search for newer, more potent and/or selective receptor ligands and drugs, there is an accompanying need for the design and development of novel highly potent and selective fluorescent ligands. Such ligands will likely aid in the investigation of the physiological and pathophysiological functions of GPCRs and also in the development of drugs acting specifically at these receptors.

The foregoing shows that there exists an unmet need for fluorescent ligands which are selective antagonists of the $A_3$ adenosine receptor.

BRIEF SUMMARY OF THE INVENTION

The present invention provides fluorescent ligands which are selective antagonists of the $A_3$ adenosine receptor.

Thus, the invention provides a compound of the formula (I):

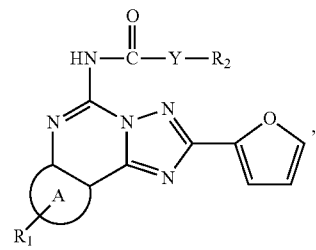

wherein:
A, together with $R_1$, is

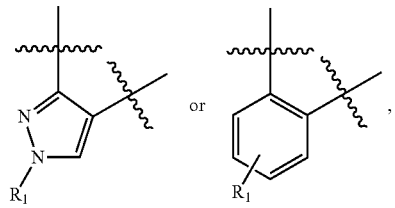

Y is

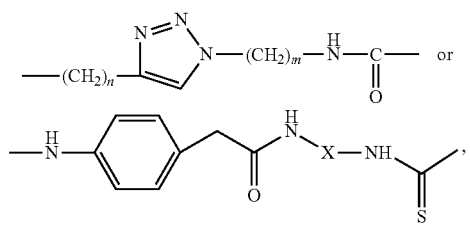

X is $(CH_2)_p$, $(CH_2CH_2O)_pCH_2CH_2$, or $CH_2CH_2CH_2O(CH_2CH_2O)_pCH_2CH_2CH_2$ $R_1$ is halo, $C_1$-$C_6$ alkyl, halo $C_1$-$C_6$ alkyl, cyano $C_1$-$C_6$ alkyl, nitro $C_1$-$C_6$ alkyl, or aryl $C_1$-$C_6$ alkyl, wherein the aryl is optionally substituted with alkyl, halo, cyano, or nitro;

$R_2$ is a fluorophore moiety;

n, m, and p are independently 1 to 6;

or a pharmaceutically acceptable salt thereof.

The invention also provides diagnostic compositions and a method of diagnosing a patient for a treatment by an antagonist of the $A_3$ adenosine receptor by the use of the compounds of the invention.

BRIEF DESCRIPTION OF THE SEVERAL VIEWS OF THE DRAWING(S)

FIG. 1 depicts the chemical structures of fluorescent antagonists in accordance with embodiments of the invention. (A) PTP and (B) TQ derivatives. The route to synthesis of TQ derivative MRS5449, 9 is also shown. Reagents and Conditions: a) 5-hexynoic acid, EDC.HCl, DMAP, $Et_3N$, an $CH_2Cl_2$:DMF (1:1, v/v), 81%; b) Alexa Fluor-4885-carboxamido-(6-azidohexanyl) bis(triethylammonium salt), aq. sodium ascorbate, aq. cupric sulfate pentahydrate solution, $H_2O$, DMF, 26%.

FIG. 2 depicts the % specific binding as a function of log [concentration] of compound 9. FIG. 2A depicts the displacement by 9 of radioligand binding to membrane preparations from CHO and HEK293 cells stably expressing hARs. Results are from one experiment representative of three independent experiments performed in duplicate. The Ki values from three experiments are listed in Table 1. FIG. 2B depicts the variation of log(dr-1) vs. log [concentration] of compound 9. The rightward-shift by MRS5449 of the concentration-response curve of the $A_3AR$ agonist Cl-IB-MECA in inhibition of forskolin-stimulated cyclic AMP production in CHO cells expressing the $A_3AR$. FIG. 2C depicts the Schild analysis of the effect of the fluorescent antagonist MRS5449 on inhibition of cyclic AMP accumulation induced by the $A_3AR$ agonist Cl-IB-MECA in CHO cells expressing the $A_3AR$. The KB value was calculated to be 4.8 nM.

FIG. 3 depicts the results of fluorescence ligand binding experiments with compounds 1-6 and 9 with FCM. $hA_3AR$-expressing CHO cells were incubated with fluorescent small molecule conjugates were used in a concentration approximately two times higher than its Ki values, and mean fluorescent intensities (MFI) of the cell-small molecule conjugates were measured with FACSCalibur flow cytometer. MFI values were converted into MESF values using QuickCal program v. 2.3 after correcting for autofluorescence. Percentages above each column show the brightness of each compound using MRS5449 set at 100%. Results are expressed as mean±S.E. (n=3).

FIG. 4 depicts the fluorescence micrographs of CHO cells expressing the $hA_3AR$ following incubation with 50 nM MRS5449 for the time as indicated: A) 15 min; B) 60 min; C) 120 min; D) 180 min. hA3AR-expressing CHO cells preincubated with 10 μM MRS1220 (E) and hA3AR-expressing CHO cells in the absence of any fluorescence ligand (F) were used as controls, but significant cell fluorescence was not observed.

FIG. 5 depicts the fluorescence binding experiments with MRS5449 using FCM in CHO cells expressing $hA_3AR$. Mean fluorescent intensities (MFI) of the cell-small molecule conjugates were measured with FACSCalibur flow cytometer. MFI values were converted into MESF values using QuickCal program v. 2.3 after correcting for autofluorescence. FIG. 5A depicts the saturation binding of MRS5449. Nonspecific binding was measured in the presence of 10 μM selective $hA_3AR$ antagonist MRS1220. The Kd value was determined to be 5.15±1.11 nM. Results are expressed as mean±S.E. (n=3). FIG. 5B depicts a histogram of the total binding (blue), nonspecific binding (red) and autofluorescence (green) of 10 nM MRS5449 to CHO cells expressing $hA_3AR$ after 90 min incubation. The histogram represents data of one of the three independent experiments. FIG. 5C depicts the association binding kinetics of MRS5449 to CHO cells expressing $hA_3AR$. CHO cells expressing $hA_3$ ARs were incubated with 10 nM MRS5449 for different time intervals. Nonspecific binding was measured in the presence of 10 μM MRS1220. The t1/2 for association was found to be 53 min. Results are expressed as mean±S.E. (n=3). FIG. 5D depicts the dissociation kinetics of MRS5449. The concentration of MRS5449 used in association and the dissociation experiments was 10 nM. Dissociation was initiated after 90 min by adding 10 μM MRS1220. Kd was found to be 6.65±0.55 nM. Results are expressed as mean±S.E. (n=3).

FIG. 6 depicts the % binding to the $A_3$ AR of CHO cells by compound 9 by itself or in the presence of known AR ligands MRS1220 and Cl-IB-MECA.

FIG. 7A depicts the results of tests conducted on known AR ligands (MRS1220, Cl-IB-MECA, NECA and DPCPX). Competitive binding assay was performed using CHO cells expressing the $hA_3AR$ incubated with 5 nM of compound 9 and increasing concentrations of the adenosine receptor ligands for 90 min at 37° C. The Ki values are (nM): 3.46±0.8; 27.7±6.3; 149±13 and 1320±60; respectively. Results are expressed as mean±S.E. (n=3). FIG. 7B depicts the displacement curve of Cl-IB-MECA using MRS5449 as a tracer. Competitive binding assay was performed using CHO cells expressing $hA_3AR$ incubated with 5 nM MRS5449 and increasing concentrations of the Cl-IB-MECA for 90 min at 37° C. The displacement curve can be best fitted in a two-site model. Results are expressed as mean±S.E. (n=2).

DETAILED DESCRIPTION OF THE INVENTION

The invention provides fluorescent ligands which are selective antagonists of the $A_3$ adenosine receptor. Thus, in accordance with an embodiment, the invention provides a compound of the formula (I):

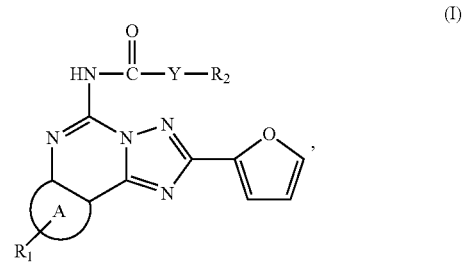

wherein:
A, together with $R_1$, is

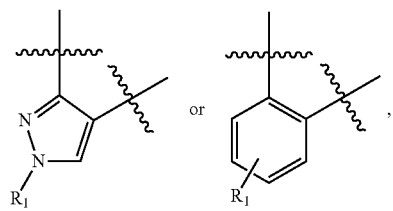

Y is

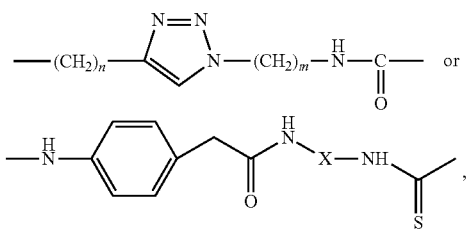

X is $(CH_2)_p$, $(CH_2CH_2O)_pCH_2CH_2$, or $CH_2CH_2CH_2O(CH_2CH_2O)_pCH_2CH_2CH_2$ $R_1$ is halo, $C_1$-$C_6$ alkyl, halo $C_1$-$C_6$ alkyl, cyano $C_1$-$C_6$ alkyl, nitro $C_1$-$C_6$ alkyl, or aryl $C_1$-$C_6$ alkyl, wherein the aryl is optionally substituted with alkyl, halo, cyano, or nitro;

$R_2$ is a fluorophore moiety;

n, m, and p are independently 1 to 6;

or a pharmaceutically acceptable salt thereof.

In an embodiment of the compound of formula (I), the invention provides a compound of formula (Ia) or (Ib):

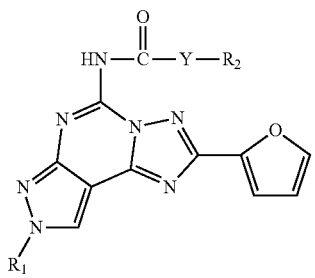

(Ia)

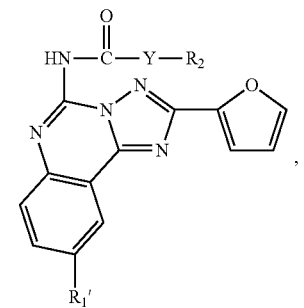

(Ib)

wherein $R_1$ is $C_1$-$C_6$ alkyl, and $R_1{'}$ is halo, $C_1$-$C_6$ alkyl, halo $C_1$-$C_6$ alkyl, cyano $C_1$-$C_6$ alkyl, nitro $C_1$-$C_6$ alkyl, or aryl $C_1$-$C_6$ alkyl, wherein the aryl is optionally substituted with alkyl, halo, cyano, or nitro.

In formula (Ia), wherein Y is

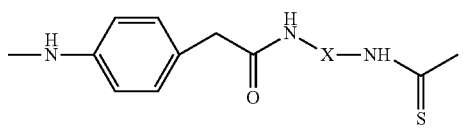

and X is $(CH_2)_p$, $(CH_2CH_2O)_pCH_2CH_2$, or $CH_2CH_2CH_2O(CH_2CH_2O)_pCH_2CH_2CH_2$.

In any of the embodiments above, p is 2, 3, 4, or 5.

In an embodiment of the compound of formula (I), the invention provides a compound of formula (IIa) or (IIb):

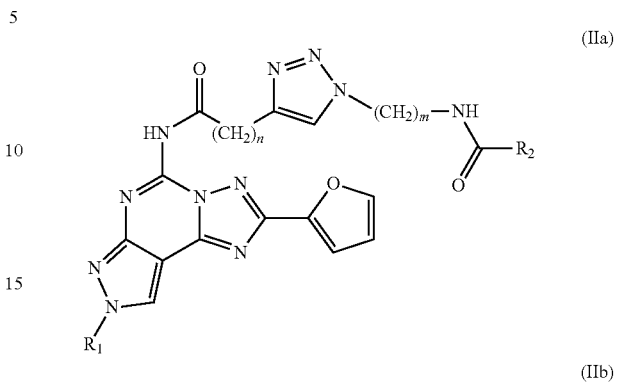

(IIa)

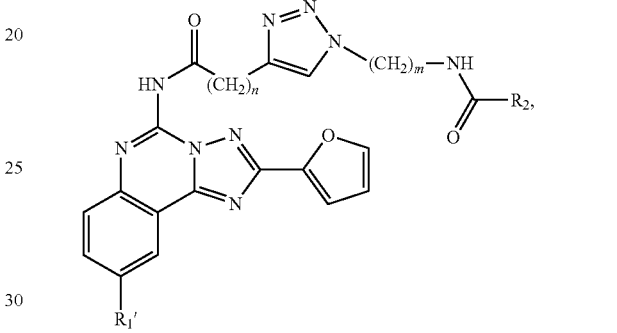

(IIb)

wherein $R_1$ and $R_1{'}$ are independently halo, $C_1$-$C_6$ alkyl, halo $C_1$-$C_6$ alkyl, cyano $C_1$-$C_6$ alkyl, nitro $C_1$-$C_6$ alkyl, or aryl $C_1$-$C_6$ alkyl, wherein the aryl is optionally substituted with alkyl, halo, cyano, or nitro;

$R_2$ is a fluorophore moiety; and n and m are independently 1 to 6.

In accordance with any of the embodiments above, $R_1$ is $C_1$-$C_6$ alkyl.

In accordance with any of the embodiments, $R_1{'}$ is halo, $C_1$-$C_6$ alkyl, halo $C_1$-$C_6$ alkyl, cyano $C_1$-$C_6$ alkyl, nitro $C_1$-$C_6$ alkyl, or aryl $C_1$-$C_6$ alkyl.

Figure 14:
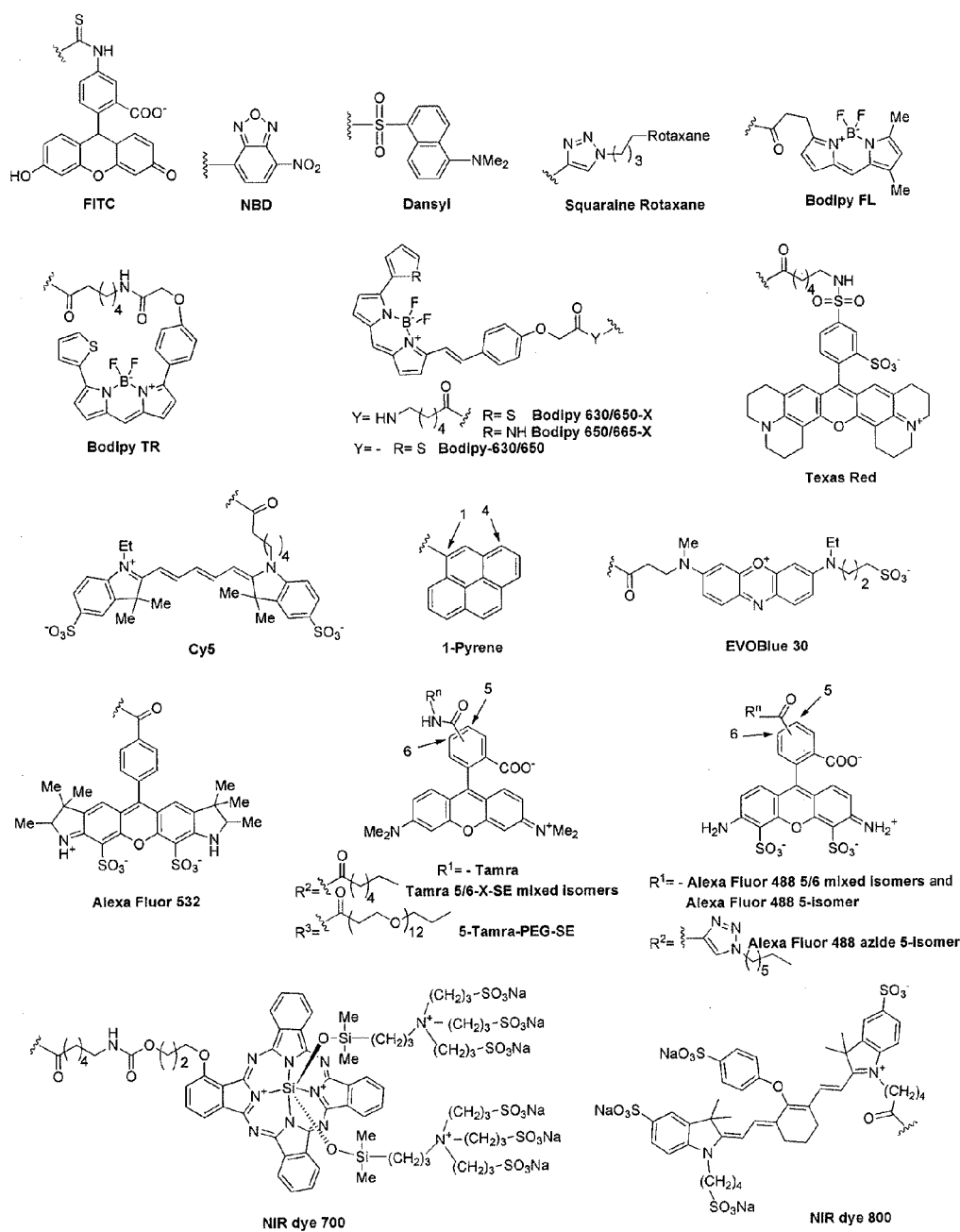
FIG. 14 depicts structures of exemplary fluorophores in accordance with embodiments of the invention.

In accordance with the invention, the fluorophore can be any suitable fluorophore, for example, an Alexa Fluor dye, a fluorescein dye, or a cyanine dye. Examples of fluorophores include FITC, NBD, Dansyl, Squaraine Rotaxane, Bodipy FL, Bodipy TR, Bodipy-630/650, Texas Red, Cy5, 1-pyrene, EVOBlue 30, Alexa Fluor 532, Alexa Fluor 488-5, 6, or mixture thereof, Tamra, Tamra 5/6-X-SE, Alexa Fluor 488 azide 5 isomer, NIR dye 700, and NIR dye 800. Additional examples of Alexa Fluor fluorophore include Alexa Fluor 350, 405, 430, 500, 514, 532, 546, 555, 568, 594, 610, 633, 647, 660, 680, 700, and 750. See FIG. 14 for structures of exemplary fluorophores including their possible points of attachment to the pharmacophore moiety.

The fluorophore moiety can be linked to Y at any of its suitable reactive site or sites through a direct reaction with a reactive group or through the use of a spacer group. For example, an FITC moiety can be linked at or through a reaction of its isothiocyanate group to an amino group on Y. A Dansyl moiety can be linked at or through a reaction of its sulfonyl chloride group to an amino group on Y. A Bodipy moiety can be linked at or through a reaction of its carboxyl group with an amino group on Y. Alexa Fluor 532 can be linked at or through a reaction of its maleimide activated benzoate group to an amino or hydroxyl group on Y.

EVOBlue 30 can be linked at or through a reaction of its carboxyl group with an amino group on Y. Alternatively, a spacer group can be employed to link the fluorophore moiety to Y. Examples of spacer groups include aminoalkyl carboxyl groups, amino alkoxy carboxyl groups, amino polyalkoxy carboxyl groups, dicarboxylic acid groups, polyamines, diamines, and the like.

In any of the embodiments, m is 4-6, for example, 6.

In any of the embodiments, n is 1-3, for example, 3.

Examples of the compounds of the invention include:

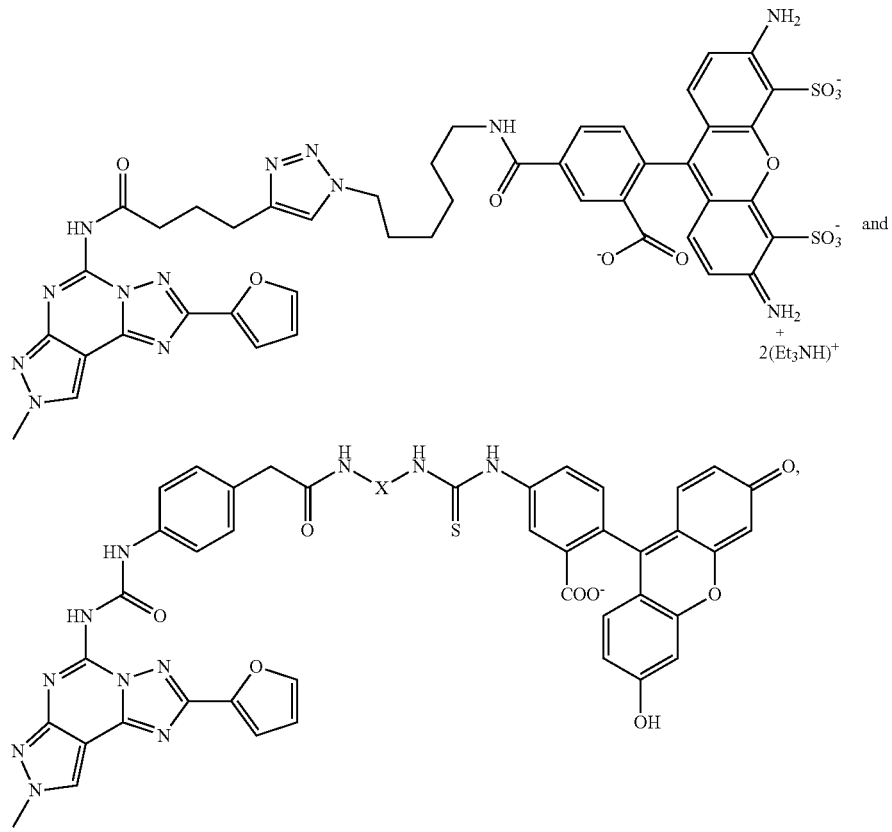

definition also applies wherever "alkyl" occurs such as in hydroxyalkyl, monohalo alkyl, dihalo alkyl, and trihalo alkyl.

The term "halo" refers to a halogen selected from the group consisting of fluorine, chlorine, bromine, and iodine, preferably chlorine or bromine.

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

Whenever a range of the number of atoms in a structure is indicated (e.g., a $C_{1-12}$, $C_{1-8}$, $C_{1-6}$, or $C_{1-4}$ alkyl), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), wherein X is $(CH_2)_p$ where p is 3, 4, or 5; or $(CH_2CH_2O)_p$ $CH_2CH_2$ or $CH_2CH_2CH_2O(CH_2CH_2O)_p CH_2CH_2CH_2$, where p is 2.

In accordance with the invention, the term "aryl" refers to a mono, bi, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise 4n+2 π electrons, according to Hackers Rule, wherein n=1, 2, or 3.

In accordance with an embodiment, the alkyl group is preferably a $C_1$-$C_3$ alkyl. Examples of alkyl group include methyl, ethyl, n-propyl, isopropyl, n-butyl, sec-butyl, isobutyl, tert-butyl, n-pentyl, isopentyl, n-hexyl, and the like. This 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

Compounds in accordance with an embodiment of the invention, e.g., PTP derivatives of varying chain length 1-6 can be prepared by coupling a fluorophore, e.g., FITC, to various chain-extended alkyl amino derivatives. Compounds 2-4 contained homologous n-alkyl spacer chains, and 5 and 6 contained multiple ether linkages. The shortest member of the series, 1, is a hydrazino derivative with no alkyl spacer chain, and the longest member, 6, contains a spacer chain of 13 atoms.

In accordance with another embodiment of the invention, derivatives of triazolo[1,5-c]quinazolin-5-yl)amine AR antagonist, CGS15943 were prepared. Click chemistry was used to label the scaffold with an analogue of fluorescein, i.e., the fluorophore Alexa Fluor-488; see, for example, Kecskes, M., et al., *Biochem Pharmacol* 2010; 80:506-11. Its spectral properties are nearly identical to those of fluorescein, over which it has many advantages for FCM experiments, e.g., photostability, brightness, relative pH-insensitivity and a relatively high Stokes shift. Click chemistry is a facile means of combining two chemical moieties, even if divergent in molecular weight or chemical properties; Moses, J. E., et al., *Chem Soc Rev* 2007; 36:1249-62. The most commonly used form of click chemistry was adopted for the synthesis of TQ derivative MRS5449, i.e. copper(I) catalyzed 3+2 cycloaddition of an azide and a terminal alkyne group. This reaction forms a triazole linkage, which is expected to be more chemical stable than the thiourea group present in the PTP derivatives 1-6 and also makes it possible to interact with potential aromatic binding residues in the outer region of the receptor binding pocket; Lenzi, O., et al., *Science* 2008; 322:1211-7.

In order to introduce the handle with a spacer arm for attachment of the Alexa Fluor-488 fluorophore, commercially available compound 7 (CGS15943) was initially condensed with 5-hexynoic acid using EDC to obtain the terminal alkyne derivative 8 in 80% yield. The fluorophore was attached to the terminal alkyne of compound 8 using click reaction conditions to obtain target conjugate MRS5449 in a yield of 26%.

Fluorescein-(Pyrazolo-triazolo-pyrimidine) conjugates (FITC-PTP) 22-26 were prepared following the general synthetic strategy summarized in Scheme 1. The carboxylic acid derivative 11 was obtained by hydrolysis in basic conditions of the previously reported[1] ureido-PTP $A_3$ adenosine receptor antagonist 10. Subsequent coupling with suitable mono-Boc protected diamines (12-16) and deprotection of the amino group lead to derivatives 17-21. Diamino chains are introduced as spacers between the pharmacophore (compound 2) and the fluorescent (FITC) moieties, in order to avoid negative interactions on the affinity at the $A_3$ adenosine receptor.

Reaction of the amino derivatives 17-21 with fluorescein isothiocyanate afforded the desired FITC-PTP compounds (22-26).

Instead 5-alkynamides derivatives of PTP (36-39) were obtained following the procedure reported in Scheme 2, by reaction of the well-known 5-amino-8-methyl-2-(2-furyl) pyrazolo[4,3-e]1,2,4-triazolo[1,5-c]pyrimidine 27 with the alkynoyl chlorides 32-35. Moro, S., et al., *J. Med. Chem.* 2005, 48, 152-162. Alkynoyl chlorides 32-35 were obtained by chlorination of the corresponding commercial available alkynoic acids 28-30 with oxalyl dichloride, while the oct-7-ynoic acid 31 was obtained as reported in literature. Nielsen, T. T., et al., *Biomacromolecules* 2010, 11, 1710-1715; Garner, A. L., et al., *Angew. Chem. Int. Ed.* 2010, 49, 9630-9634.

The present invention further provides a diagnostic composition comprising a compound or salt as described above and a pharmaceutically acceptable carrier. The present invention further provides a diagnostic method for determining a treatment of a patient for a possible antagonist of the $A_3$ adenosine receptor, the treatment comprising:

(a) administering a compound or salt as described above;
(b) obtaining a biological sample from the patient;
(c) determining the level of expression of $A_3$ adenosine receptor in the biological sample;
(d) comparing the level of expression of the $A_3$ adenosine receptor to that of a normal population; and
(e) if the patient's level of expression is higher than that of the normal population, determining a treatment regimen comprising administering an antagonist of the $A_3$ adenosine receptor whose expression was higher in the patient than that of the normal population.

Embodiments of the invention include a process for preparing compositions comprising the compounds of the present invention and a carrier. With respect to compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active compounds, and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

The choice of carrier will be determined, in part, by the particular compound used in the composition, as well as by the particular method used to administer the composition. Accordingly, there are a variety of suitable formulations of the composition of the invention. The following formulations for parenteral, subcutaneous, intravenous, intramuscular, intraarterial, intrathecal and interperitoneal administration are exemplary, and are in no way limiting. More than one route can be used to administer the compositions of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the compounds of the present invention, administered should be sufficient to effectively target the cell or population of cells in vivo, such that the fluorescence resulting from the binding of the compounds to the cells and their subsequent cleavage, provides a fluorescent signal that can be detected, in the subject over a reasonable time frame. The dose will be determined by the efficacy of the particular compound and the location of the target population of cells in the subject, as well as the body weight of the subject to be treated.

The dose of the compound of the present invention also will be determined by the existence, nature and extent of any adverse side effects that might accompany the administration of a particular compound. Typically, an attending physician will decide the dosage of the compound with which to treat each individual subject, taking into consideration a variety of factors, such as age, body weight, general health, diet, sex, compound to be administered, route of administration, and the severity of the condition being treated. By way of example, and not intending to limit the invention, the dose of the imaging agent can be about 0.001 to about 1000 mg/kg body weight of the subject being treated or diagnosed, from about 0.01 to about 10 mg/kg body weight, and from about 0.1 mg to about 1 mg/kg body weight.

The compounds of the present invention may also include incorporation of the active ingredients into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

The $A_3$ AR is found in the central nervous system (CNS), brain, testes, eyes, and the immune system, where it appears to be involved in the modulation of release from mast cells of mediators of the immediate hypersensitivity reaction (Ramkumar et al., *J. Biol. Chem.*, 268, 16887-16890 (1993)). $A_3$ AR selective antagonists serve as cerebroprotective, antiasthmatic, and/or anti-inflammatory agents or anti-glaucoma agents for reducing intraocular pressure. See, e.g., U.S. Pat. Nos. 6,066,642 and 6,528,516 and WO 2008/055711. The compounds of the invention can be used to diagnose and/or monitor the tissues and diseases of the central nervous system (CNS), brain, testes, eyes, and the immune system. For example, the compounds of the invention can be used to monitor the condition of the eye and diagnose a treatment with an $A_3$ AR selective antagonist, for example, for reducing the intraocular pressure. The $A_3$ AR is also overexpressed in various forms of cancer and inflammation; Ochaion, A., et al., supra; Gessi, S., et al., *Expert Opin Investig Drugs* 2011; 20: 1591-609; and in peripheral blood mononuclear cells; Gessi, S., et al., *Clin Cancer Res* 2004; 10: 5895-901. Thus, the compounds of the invention can be used to monitor various forms of cancers, including colorectal cancer, and rheumatoid arthritis.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

As used herein, the term "detection" or "imaging" or means the use of certain properties of fluorescent molecules or dyes and the light emitted from the excited fluorescent dye to diagnose or treat various medical conditions. Without being limited to any particular theory, in an embodiment of the present invention, a compound of the present invention is injected intravenously into the subject which then concentrates in the target cells or organ of interest. By placing a camera that senses the emitted light from the fluorescent dye at the proper emission wavelength over the body, an image of the target cells or organ of interest can be created. The compounds of the present invention can be detected by suitable devices such as fluorimeters, spectrophotometric detectors, cameras and the like, preferably a near-infrared intraoperative fluorescence imaging system.

Abbreviations: AF488—Alexa Fluor-488; CHO—Chinese hamster ovary; CGS15943—N-[9-chloro-2-(2-furanyl) [1,2,4]triazolo[1,5-c]quinazolin-5-amine; CGS21680—2-

[p-(2-carboxyethyl)phenylethylamino]-5'-N-ethylcarboxamido-adenosine; Cl-IB-MECA—1-[2-chloro-6-[[(3-iodophenyl)methyl]amino]-9H-purin-9-yl]-1-deoxy-N-methyl-β-D-ribofuranuronamide; CPA—(2R,3R,4S,5R)-2-[6-(cyclopentylamino)purin-9-yl]-5(hydroxymethyl) oxolane-3,4-diol; DMAP—4-dimethylaminopyridine; DMEM—Dulbecco's Modified Eagle Medium; DMF—N,N-dimethylformamide; DMSO—dimethyl sulfoxide; PBS—phosphate buffered saline; DPCPX—8-cyclopentyl-1,3-dipropylxanthine; EDC—1-ethyl-[3-dimethylaminopropyl] carbodiimide; EDTA—ethylenediaminetetraacetic acid; EL—extracellular loop; FBS—fetal bovine serum; FCM—flow cytometry; FITC—fluorescein isothiocyanate; GPCR—G protein-coupled receptor; HEK—human embryonic kidney; [$^{125}$I]I-AB-MECA—[$^{125}$I]4-amino-3-iodobenzyl-5'-N-methylcarboxamidoadenosine; IB-MECA—1-Deoxy-1-[6-[[(3-iodophenyl)methyl]amino]-9H-purin-9-yl]-N-methyl-β-D-ribofuranuronamide; MD—molecular dynamics; MESF—molecules of equivalent soluble fluorochrome; MOE—Molecular Operating Environment; MFI—measured fluorescent intensity; MRS1220—N-[9-chloro-2-(2-furanyl)[1,2,4]-triazolo[1,5-c]quinazolin-5-yl]benzene acetamide; MRS5346—5-((2-(2-(4-(3-(5-amino-2-(furan-2-yl)-7H-pyrazolo[4,3-e][1,2,4]triazolo[1,5-c]pyrimidin-7-yl) propyl)phenoxy)acetamido)-ethyl)carbamoyl)-2-(6-amino-3-iminio-4,5-disulfonato-3H-xanthen-9-yl)benzoate; MRS5449—2-(6-amino-3-iminio-4,5-disulfonato-3H-xanthen-9-yl)-5-((6-(4-(4-((9-chloro-2-(furan-2-yl)-[1,2,4]triazolo[1,5-c]quinazolin-5-yl)amino)-4-oxobutyl)-1H-1,2,3-triazol-1-yl)hexyl)carbamoyl)benzoate; NECA—5'-N-ethylcarboxamidoadenosine; PSB10—8-ethyl-1,4,7,8-tetrahydro-4-methyl-2-(2,3,5-trichlorophenyl)-5H-imidazo [2,1-i]purin-5-one monohydrochloride; TM—transmembrane helix; XAC—xanthine amine congener, N-(2-aminoethyl)-2-[4-(2,3,6,7-tetrahydro-2,6-dioxo-1,3-dipropyl-1H-purin-8-yl)phenoxy]-acetamide hydrochloride; ZM241385—4-(2-[7-amino-2-(2-furyl)[1,2,4]triazolo [2,3-a][1,3,5]triazin-5-ylamino]ethyl)phenol.

The following examples further illustrate the invention but, of course, should not be construed as in any way limiting its scope.

EXAMPLE 1

This example illustrates methods of preparing compounds in accordance with an embodiment of the invention.

Materials and Methods

Alexa Fluor-488 5-carboxamido-(6-azidodhexanyl)bis (triethylammonium salt) was purchased from Invitrogen (Carlsbad, Calif.). [$^3$H]R—N$^6$-(2-phenylisopropyl)adenosine ([$^3$H]R-PIA, 42.6 Ci/mmol) was obtained from Moravek Biochemicals (Brea, Calif.). [$^{125}$I]4-Amino-3-iodobenzyl-5'-N-methylcarboxamidoadenosine ([$^{125}$I]I-AB-MECA, 2200 Ci/mmol), and [$^3$H]-2-[p-(2-carboxyethyl)phenylethylamino]-5'-N-ethylcarboxamido-adenosine ([$^3$H] CGS21680, 40.5 Ci/mmol) were purchased from Perkin Elmer (Waltham, Mass.). DMEM/F12 medium and 1 M Tris-HCl (pH 7.5) were purchased from Mediatech, Inc. (Herndon, Va.). Adenosine deaminase, Cl-IB-MECA and NECA were from Sigma (St. Louis, Mo.). CGS15943, CGS21680, CPA, DPCPX, IB-MECA, MRS1220, PSB10, XAC and ZM241385 were from Tocris (Ellisville, Mo.). Quantum Alexa Fluor-488 MESF beads were purchased from Bangs Laboratories, Inc. (Fishers, Ind.). All other reagents were from Sigma-Aldrich (St. Louis, Mo.), unless noted, and were of analytical grade and used without further purification.

Synthesis of Compounds 1-6

General methods for preparing compounds 1-6: Reactions were conducted under an atmosphere of argon whenever anhydrous solvents were used. All reactions were monitored by thin-layer chromatography (TLC) using silica gel coated plates with a fluorescence indicator (Sigma-Aldrich, St. Louis, Mo.), which was visualized under UV light. Silica gel column chromatography was performed with silica gel (SiO$_2$, 200-400 mesh, 60 Å, Sigma-Aldrich, St. Louis, Mo.) using moderate air pressure. Evaporation of solvents was carried out under reduced pressure at a temperature below 40° C. After column chromatography, appropriate fractions were pooled, evaporated and dried at high vacuum for at least 12 h to give the desired products in high purity. $^1$H NMR and analytical HPLC ascertained sample purity. No corrections in yield were made for solvent of crystallization. $^1$H NMR spectra were recorded at 400 MHz. Chemical shifts are reported in parts per million (ppm) relative to tetramethylsilane or deuterated solvent as the internal standard ($\delta_H$: CDCl$_3$ 7.26 ppm). High resolution mass spectroscopic (HRMS) measurements were performed on a proteomics optimized Q-TOF-2 (Micromass-Waters) using external calibration with polyalanine. Observed mass accuracies are those expected on the basis of known performance of the instrument as well as the trends in masses of standard compounds observed at intervals during the series of measurements. Reported masses are observed masses uncorrected for this time-dependent drift in mass accuracy.

N-(9-Chloro-2-(furan-2-yl)-[1,2,4]triazolo[1,5-c] quinazolin-5-yl)hex-5-ynamide (8). Compound 7 (11.2 mg, 39.2 μmol) was co-evaporated with anhydrous toluene (2×5 ml) and dissolved in anhydrous CH$_2$Cl$_2$: N,N'-dimethylformamide (1 ml, 1:1, v/v). 1-Ethyl-[3-dimethylaminopropyl] carbodiimide hydrochloride (EDC.HCl, 45 mg, 235 μmol, 5-hexynoic acid (26 μl, 235 μmol), 4-dimethylaminopyridine (2 mg, 15.6 μmol) and triethylamine (82 μl, 588 μmol) were added. The reaction mixture was stirred for 22 h whereupon it was diluted with CH$_2$Cl$_2$ (30 ml) and sequentially washed with brine (2×10 ml) and distilled water (2×10 ml). The organic phase was evaporated to dryness and the resulting residue purified by silica gel column chromatography (0-25% acetone in hexane, v/v) to afford compound 8 as a white solid (12.1 mg, 81%). R$_f$=0.5 (30% acetone in hexane, v/v); MALDI-HRMS m/z 380.0919 ([M+H]$^+$, C$_{19}$H$_{14}$N$_5$O$_2$Cl.H$^+$ Calcd 380.0914); Selected signals: $^1$ H NMR (CDCl$_3$) δ 9.03 (s, 1H), 8.51 (d, J=2.3 Hz, 1H), 7.91 (d, J=8.8 Hz, 1H), 7.76 (dd, J=8.8 & 2.3 Hz, 1H), 7.70 (s, 1H), 7.33 (d, J=3.5 Hz, 1H), 6.64-6.67 (m, 1H), 3.25 (t, J=7.3 Hz, 2H), 2.42-2.48 (m, 2H), 2.03-2.13 (m, 3H). Analytical purity of compound 8 was determined using a Hewlett-Packard 1100 HPLC equipped with a Zorbax SB-Aq 5 μm analytical column (50×4.6 mm; Agilent Technologies Inc, Palo Alto, Calif.). Mobile phase: linear gradient solvent system: 5 mM TBAP (tetrabutylammonium dihydrogen phosphate)-CH$_3$CN from 80:20 to 40:60 in 13 min; the flow rate was 0.5 ml/min. Peaks were detected by UV absorption with a diode array detector at 254, 275, and 280 nm. Purity>99% by HPLC (retention time: 10.43 min).

2-(6-Amino-3-iminio-4,5-disulfonato-3H-xanthen-9-yl)-5-((6-(4-(4-((9-chloro-2-(furan-2-yl)-[1,2,4]triazolo[1,5-c]quinazolin-5-yl)amino)-4-oxobutyl)-1H-1,2,3-triazol-1-yl)hexyl)carbamoyl)benzoate (9, MRS5449)

A solution of Alexa Fluor-488 5-carboxamido-(6-azidohexanyl)bis(triethylammonium salt) (0.5 mg, 0.58 μmol, Invitrogen-Life Technologies, Grand Island, N.Y.) in H$_2$O (200 μl) was added to a solution of alkyne 8 (0.44 mg, 1.1 μmol) in N,N'-dimethylformamide (100 μl). A freshly prepared solution of aqueous sodium ascorbate (0.1 M, 8 μl, 5.86 μmol) was added to the reaction mixture followed by addition of aqueous cupric sulfate pentahydrate solution (0.1 M, 2.94 μl, 0.29 μmol). The resulting mixture was stirred overnight at room temperature; 10 mM aqueous solution of triethylammonium acetate buffer (2 ml) was added with constant mixing. The resulting mixture was lyophilized and purified by HPLC with a Luna 5μ RP-C18 semipreparative column (250×10.0 mm; Phenomenex, Torrance, Calif.) under the following conditions: flow rate of 2 ml/min; $H_2O$—$CH_3CN$ from 100:0 (v/v) to 0:100 (v/v) in 30 min and isolated at 20.07 min to get Alexa Fluor-488 conjugate 9 (0.16 mg, 27%). ESI-HRMS m/z 1036.1957 [M+Na]+, $C_{46}H_{38}N_{11}O_{12}S_2Cl.H+$: Calcd. 1036.1910. Analytical purity>99% by HPLC (retention time: 10.13 min).

General methods for preparing compounds 11-39: Reactions were routinely monitored by thin-layer chromatography (TLC) on silica gel (precoated F254 Merck plates). Flash chromatography was performed using Merck 60-200 mesh silica gel. Light petroleum ether refers to the fractions boiling at 40-60° C. Melting points were determined on a Buchi-Tottoli instrument and are uncorrected. $^1$H-NMR were determined in $CDCl_3$, DMSO-$d_6$ or $CD_3OD$ solutions with a Varian Gemini 200, a Bruker 400 or a Varian 500 spectrometers. Peaks positions are given in parts per million (δ) downfield relative to the central peak of the solvents, and J values are given in Hz. The following abbreviations were used: s, singlet; bs, broad singlet; d, doublet; dd, double doublet; bd, broad doublet; t, triplet; m, multiplet. Electrospray mass spectra were recorded on a ESI Bruker 4000 Esquire spectrometer and compounds were dissolved in methanol. Absorption experiments were performed on a Varian Cary 5000 spectrophotometer. Fluorescence measurements were recorded on Varian Cary Eclipse fluorescence spectrophotometer, with excitation filter at 361 nm, emission filter at 390-600 nm (all experiments were performed using a $\lambda_{ex}$ of 488 nm). Oct-7-ynoic acid was synthesized as reported in literature. Garner, A. L., et al., supra.

Procedure for the synthesis of 2-(4-(3-(2-(furan-2-yl)-8-methyl-8H-pyrazolo[4,3-e][1,2,4]triazolo[1,5-c]pyrimidin-5-yl)ureido)phenyl)acetic acid (11). Ethyl ester derivative 10 (1.95 mmol, 900 mg) was dissolved in a mixture of tetrahydrofuran/methanol/water (4:1:1, 12 mL) and lithium hydroxide monohydrate (5.9 mmol, 245 mg) was added. The suspension was stirred at room temperature overnight. Reaction was monitored by TLC (ethyl acetate 9.5/methanol 0.5). Water was added to the mixture, the solution was cooled to 0° C. and hydrochloric acid was added (pH 2) since a pale brown solid precipitated. Solid was filtered and washed with ethyl ether leading to the desired compound in a quantitative yield. Mp>300° C.; $^1$H-NMR (200 MHz, DMSO-$d_6$) δ 10.67 (s, 1H) 9.55 (bs, 1H), 8.78 (s, 1H), 7.93 (s, 1H) 7.78-7.36 (m, 3H), 7.38-6.96 (m, 3H), 6.76 (bs, 1H), 4.34 (s, 3H), 3.56 (s, 2H). MS-ESI (methanol) m/z 431.0 (M−1).

General procedure for the synthesis of amides 12-16. The carboxylic acid derivative 11 (0.5782 mmol, 250 mg) was dissolved in DMF (3 mL) and the appropriate monoBoc-protected diamine was added (0.5782 mmol). Reaction was stirred and cooled to 0° C. under an argon atmosphere and then 1-ethyl-3-(3-dimethylaminopropyl)carbodiimmide hydrochloride (EDCI.HCl, 1.1564 mmol, 221.7 mg) and 4-dimethylaminopyridine (DMAP, 1.4455 mmol, 176.6 mg) were added. The mixture was stirred at room temperature overnight and monitored by TLC (dichloromethane 9.3/methanol 0.7). The solvent was evaporated under vacuum.

The residue was suspended in water and extracted with ethyl acetate (3 times). The organic layer was dried over sodium sulfate and the solvent evaporated. The crude was purified on flash silica column chromatography (dichloromethane 9.7/methanol 0.3) to give the desired compounds (12-16).

tert-Butyl (3-(2-(4-(3-(2-(furan-2-yl)-8-methyl-8H-pyrazolo[4,3-e][1,2,4]triazolo[1,5-c]pyrimidin-5-yl)ureido)phenyl)acetamido)propyl)carbamate (12).

Yield 29.40%; white solid; mp 198-205° C.; $^1$H-NMR (200 MHz, $CDCl_3$) δ 11.19 (s, 1H), 8.60 (s, 1H), 8.23 (s, 1H), 7.80-7.46 (m, 3H), 7.30-7.26 (m, 3H), 6.62 (dd, J=3.4, 1.8 Hz, 1H), 6.05 (bs, 1H), 4.94 (bs, 1H), 4.21 (s, 3H), 3.58 (s, 2H), 3.27 (q, J=6 Hz, 2H), 3.15-3.00 (m, 2H), 1.56 (t, J=6, 2H), 1.42 (s, 9H); MS-ESI (methanol) m/z 611.3 (M+23).

tert-Butyl (4-(2-(4-(3-(2-(furan-2-yl)-8-methyl-8H-pyrazolo[4,3-e][1,2,4]triazolo[1,5-c]pyrimidin-5-yl)ureido)phenyl)acetamido)butyl)carbamate (13).

Yield 34.46%; white solid; mp 186-193° C.; $^1$H-NMR (200 MHz, $CDCl_3$) δ 11.19 (s, 1H), 8.60 (s, 1H), 8.22 (s, 1H), 7.90-7.48 (m, 3H), 7.38-7.09 (m, 3H), 6.62 (s, 1H), 5.63 (bs, 1H), 4.60 (bs, 1H), 4.21 (s, 3H), 3.57 (s, 2H), 3.22 (bs, 2H), 3.09 (bs, 2H), 1.75 (bs, 4H), 1.43 (s, 9H); MS-ESI (methanol) m/z 625.4 (M+23), 641.3 (M+39).

tert-Butyl (5-(2-(4-(3-(2-(furan-2-yl)-8-methyl-8H-pyrazolo[4,3-e][1,2,4]triazolo[1,5-c]pyrimidin-5-yl)ureido)phenyl)acetamido)pentyl)carbamate (14).

Yield 28%; white solid; mp 78-185° C.; $^1$H-NMR (200 MHz, $CDCl_3$) δ 11.20 (s, 1H), 8.61 (s, 1H), 8.23 (s, 1H), 7.66 (bs, 3H), 7.26 (bs, 3H), 6.62 (bs, 1H), 5.47 (bs, 1H), 4.56 (bs, 1H), 4.21 (s, 3H), 3.57 (s, 2H), 3.20 (bs, 2H), 3.07 (bs, 2H), 1.60-1.10 (m, 15H); MS-ESI (methanol) m/z 639.4 (M+23), 655.3 (M+39).

tert-Butyl (2-(2-(2-(2-(4-(3-(2-(furan-2-yl)-8-methyl-8H-pyrazolo[4,3-e][1,2,4]triazolo[1,5-c]pyrimidin-5-yl)ureido)phenyl)acetamido)-ethoxy)ethoxy)ethyl)carbamate (15).

Yield 54%; white solid; mp 157-165° C.; $^1$H-NMR (200 MHz, $CDCl_3$) δ 11.18 (s, 1H), 8.60 (s, 1H), 8.23 (s, 1H), 7.78-7.56 (m, 3H), 7.42-7.15 (m, 3H), 6.62 (dd, J=3.2, 1.6 Hz, 1H), 5.97 (bs, 1H), 5.02 (bs, 1H), 4.22 (s, 3H), 3.73-3.35 (m, 12H), 3.29 (bs, 2H), 1.42 (s, 9H); MS-ESI (methanol) m/z 685.4 (M+23), 701.4 (M+39).

tert-Butyl (1-(4-(3-(2-(furan-2-yl)-8-methyl-8H-pyrazolo[4,3-e][1,2,4]triazolo[1,5-c]pyrimidin-5-yl)ureido)phenyl)-2-oxo-7,10,13-trioxa-3-azahexadecan-16-yl)carbamate (16).

Yield 21.60%; white solid; mp 151-158° C.; $^1$H-NMR (270 MHz, $CDCl_3$) δ 11.19 (s, 1H), 8.60 (s, 1H), 8.24 (s, 1H), 7.80-7.61 (m, 3H), 7.45-7.19 (m, 3H), 6.63 (bs, 1H), 6.20 (bs, 1H), 4.96 (bs, 1H), 4.22 (s, 3H), 3.71-3.49 (m, 14H), 3.35 (bs, 2H), 3.20 (bs, 2H), 1.73 (t, J=3.2, 4H), 1.49 (s, 9H); MS-ESI (methanol) m/z 757.4 (M+23).

General synthesis of compounds 17-21 by N-Boc deprotection. The N-Boc protected derivatives (12-16) were dissolved in a solution of TFA and dichloromethane (1:1) and the mixtures were stirred for 2 hours at room temperature. Reactions were monitored by TLC (dichloromethane 9.3/methanol 0.7). The solvent was removed under vacuum and the solids were filtered to give the desired compounds (17-21).

N-(3-aminopropyl)-2-(4-(3-(2-(furan-2-yl)-8-methyl-8H-pyrazolo[4,3-e][1,2,4]triazolo[1,5-c]pyrimidin-5-yl)ureido)phenyl)acetamide trifluoroacetate salt (17).

Yield 89.75%; white solid; mp 142-150° C.; $^1$H-NMR (200 MHz, $CD_3OD$) δ 11.28 (s, 1H), 8.48 (s, 1H), 8.31 (bs, 1H), 7.76 (s, 1H), 7.62 (d, J=8.2 Hz, 2H), 7.30 (d, J=8.2 Hz, 1H), 7.24 (d, J=3.4 Hz, 1H) 6.66 (bs, 1H), 4.15 (s, 3H), 3.52 (s, 2H), 3.34-3.10 (m, 2H), 2.89 (t, J=7.0 Hz, 2H), 1.85 (p, J=7.0 Hz, 2H).

N-(4-Aminobutyl)-2-(4-(3-(2-(furan-2-yl)-8-methyl-8H-pyrazolo[4,3-e][1,2,4]triazolo[1,5-c]pyrimidin-5-yl)ureido)phenyl)acetamide trifluoroacetate salt (18).

Yield 95.11%; white solid; mp 167-173° C.; $^1$H-NMR (200 MHz, CD$_3$OD) δ 8.48 (s, 1H), 8.19 (bs, 1H), 7.76 (s, 1H), 7.63 (d, J=8.2 Hz, 2H), 7.39-7.13 (m, 3H), 6.70-6.62 (m, J=1H), 4.14 (s, 3H), 3.51 (s, 2H), 3.32-3.30 (m, 2H), 2.92 (t, J=6.7 Hz, 2H), 1.78-1.49 (m, 4H).

N-(5-aminopentyl)-2-(4-(3-(2-(furan-2-yl)-8-methyl-8H-pyrazolo[4,3-e][1,2,4]triazolo[1,5-c]pyrimidin-5-yl)ureido)phenyl)acetamide trifluoroacetate salt (19).

Yield 85.27%; white solid; mp 170-178° C.; $^1$H-NMR (200 MHz, CD$_3$OD) δ 8.47 (s, 1H), 8.13 (bs, 1H), 7.75 (s, 1H), 7.61 (d, J=7.7 Hz, 2H), 7.29 (d, J=7.7 Hz, 2H), 7.25 (s, 1H), 6.66 (s, 1H), 4.14 (s, 3H), 3.49 (s, 2H), 3.33-3.08 (m, 2H), 2.88 (t, J=7.3 Hz, 2H), 1.77-1.47 (m, 4H), 1.47-1.25 (m, 2H).

2-(2-(2-(2-(4-(3-(2-(furan-2-yl)-8-methyl-8H-pyrazolo[4,3-e][1,2,4]triazolo[1,5-c]pyrimidin-5-yl)ureido)phenyl)acetamido) ethoxy)ethoxy)ethanamine trifluoroacetate salt (20). Yield 83.28%; white solid; mp 152-160° C.; $^1$H-NMR (200 MHz, CD$_3$OD) δ 8.49 (s, 1H), 8.15 (bs, 1H), 7.76 (bs, 1H), 7.62 (d, J=7.3 Hz, 2H), 7.44-7.13 (m, 3H), 6.66 (bs, 1H), 4.15 (s, 3H), 3.85-3.38 (m, 12H), 3.09 (bs, 2H); MS-ESI (methanol) m/z 563.3 (M+1), 585.3 (M+23).

N-(3-(2-(2-(3-aminopropoxy)ethoxy)ethoxy)propyl)-2-(4-(3-(2-(furan-2-yl)-8-methyl-8H-pyrazolo[4,3-e][1,2,4]triazolo[1,5-c]pyrimidin-5-yl)ureido)phenyl)acetamide trifluoroacetate salt (21). Yield 94.15%; white solid; mp 133-140° C.; $^1$H-NMR (270 MHz, CDCl$_3$) δ 11.13 (s, 1H), 8.28 (s, 1H), 7.81 (bs, 2H), 7.66 (s, 1H), 7.60 (d, J=7.7 Hz, 2H), 7.41-7.13 (m, 3H), 6.62 (s, 1H), 5.40 (bs, 2H), 4.21 (s, 3H), 3.75 (s, 2H), 3.66-3.54 (m, 12H), 3.36 (bs, 2H), 3.24 (bs, 2H), 2.02 (bs, 2H), 1.78 (bs, 2H).

General Synthesis of Fluorescein Conjugates (22-26). 0.0775 mmol of amino derivatives 17-21 were dissolved in 4 mL of dry methanol. 21.6 μL (0.155 mmol) of TEA were added to the solution which was stirred at room temperature for 30 minutes under an argon atmosphere. Then 30.2 mg (0.075 mmol) of FITC were added and the reaction was stirred for 72 hours in the dark (TLC: dichloromethane 9/methanol 1). The products were purified by column chromatography starting with dichloromethane 9/methanol 1 as eluent. The obtained solids were suspended in dichloromethane, filtered and washed several times with ethyl ether yielding to the desired compounds as an orange solids (22-26).

N-(3-(3-(Fluorescein-5-yl)thioureido)propyl)-2-(4-(3-(2-(furan-2-yl)-8-methyl-8H-pyrazolo[4,3-e][1,2,4]triazolo[1,5-c]pyrimidin-5-yl)ureido)phenyl)acetamide (22).

Yield 54.65%; orange solid; mp 198-204° C.; $^1$H-NMR (200 MHz, DMSO-d$_6$) δ 10.69 (s, 1H), 10.09 (bs, 3H), 8.76 (s, 1H), 8.41-8.05 (m, 3H), 7.98 (s, 1H), 7.76 (d, J=3.2 Hz, 1H), 7.50 (d, J=7.4 Hz, 2H), 7.39-7.03 (m, 4H), 6.76 (s, 1H), 6.65-6.47 (m, 6H), 4.12 (s, 3H), 3.50 (bs, 2H), 3.35 (s, 2H), 3.15 (bs, 2H), 1.71 (bs, 2H); $^{13}$C-NMR (50 MHz, DMSO-d$_6$) δ 180.29, 170.29, 168.44, 160.06, 159.79, 154.77, 152.93, 151.98, 151.93, 151.91, 149.57, 149.52, 148.96, 148.89, 145.30, 144.99, 141.23, 140.14, 136.60, 131.29, 129.65, 129.59, 129.49, 12923, 129.20, 129.16, 129.13, 129.01, 126.24, 124.15, 118.95, 112.68, 112.54, 112.18, 109.81, 102.17, 98.68, 45.69, 41.86, 41.44, 36.37, 28.73; UV-VIS λ$_{max}$ 523 nm; Fluorescence λ$_{em}$ 537; MS-ESI (methanol) m/z 878.3 (M+1), 900.3 (M+23), 916.3 (M+39).

N-(4-(3-(Fluorescein-5-yl)thioureido)butyl)-2-(4-(3-(2-(furan-2-yl)-8-methyl-8H-pyrazolo[4,3-e][1,2,4]triazolo[1,5-c]pyrimidin-5-yl)ureido)phenyl)acetamide (23).

Yield 53.77%; orange solid; mp 200-207° C.; $^1$H-NMR (200 MHz, DMSO-d$_6$) δ 10.72 (s, 1H), 10.06 (bs, 3H), 8.74 (s, 1H), 8.26 (bs, 2H), 8.07 (bs, 1H), 7.96 (s, 1H), 7.76 (d, J=6.9 Hz, 1H), 7.50 (d, J=8.0 Hz, 2H), 7.35-7.08 (m, 4H), 6.75 (s, 1H), 6.70-6.37 (m, 6H), 5.76 (s, 1H), 4.11 (s, 3H) 3.36 (s, 2H), 3.08 (bs, 4H), 1.51 (bs, 4H); $^{13}$C-NMR (50 MHz, DMSO-d$_6$) 180.21, 169.96, 168.47, 160.33, 160.10, 154.46, 153.01, 152.94, 152.43, 152.19, 149.96, 149.86, 148.88, 148.81, 145.30, 145.03, 141.33, 140.40, 136.61, 131.40, 129.44, 129.10, 129.04, 129.02, 126.20, 124.23, 118.98, 112.94, 112.91, 112.45, 112.16, 109.88, 102.25, 98.62, 45.76, 43.43, 41.85, 38.10, 26.82, 25.84; UV-VIS λ$_{max}$ 524 nm; Fluorescence λ$_{em}$ 535; MS-ESI (methanol) m/z 892.4 (M+1), 914.3 (M+23), 930.3 (M+29).

N-(5-(3-(Fluorescein-5-yl)thioureido)pentyl)-2-(4-(3-(2-(furan-2-yl)-8-methyl-8H-pyrazolo[4,3-e][1,2,4]triazolo[1,5-c]pyrimidin-5-yl)ureido)phenyl)acetamide (24).

Yield 28%; orange solid; mp 190-200° C.; $^1$H-NMR (200 MHz, DMSO-d$_6$) δ 10.73 (s, 1H), 10.13 (bs, 1H), 8.75 (s, 1H), 8.27 (bs, 2H), 8.11-7.87 (m, 2H), 7.76 (d, J=5.6 Hz, 1H), 7.50 (d, J=6.3 Hz, 2H), 7.39-7.02 (m, 4H), 6.75 (s, 1H), 6.71-6.39 (m, 6H), 4.12 (s, 3H), 3.38 (s, 2H), 3.07 (bs, 4H), 1.74-1.10 (m, 4H), 1.08-0.75 (m, 2H); $^{13}$C-NMR (50 MHz, DMSO-d$_6$) δ 180.17, 169.90, 168.45, 160.02, 159.91, 154.73, 152.99, 151.96, 149.80, 149.77, 148.92, 148.88, 145.24, 145.03, 141.35, 140.32, 136.63, 131.37, 129.49, 129.44, 129.27, 129.23, 129.02, 129.00, 126.21, 124.08, 119.27, 118.92, 112.94, 112.88, 112.85, 112.46, 112.18, 109.86, 102.17, 98.64, 43.74, 41.84, 40.61, 40.20, 28.79, 28.03, 23.88; UV-VIS λ$_{max}$ 523 nm; Fluorescence λ$_{em}$ 537; MS-ESI (methanol) m/z 928.4 (M+23).

N-(2-(2-(2-(3-(Fluorescein-5-yl)thioureido)ethoxy)ethoxy)ethyl)-2-(4-(3-(2-(furan-2-yl)-8-methyl-8H-pyrazolo[4,3-e][1,2,4]triazolo[1,5-c]pyrimidin-5-yl)ureido)phenyl)acetamide (25). Yield 54.32%; orange solid; mp 182-185° C.; $^1$HNMR $^1$H-NMR (200 MHz, DMSO-d$_6$) δ 10.72 (s, 1H), 10.14 (bs, 3H), 8.75 (s, 1H), 8.30 (s, 1H), 8.13 (d, J=5.0 Hz, 2H), 7.95 (s, 1H), 7.76 (d, J=7.7 Hz, 1H), 7.49 (d, J=7.9 Hz, 2H), 7.37-7.07 (m, 4H), 6.74 (s, 1H), 6.69-6.42 (m, 6H), 4.11 (s, 314), 3.79-3.48 (m, 8H), 3.51-2.86 (m, 6H); $^{13}$C-NMR (50 MHz, DMSO-d$_6$) δ 180.47, 170.26, 168.54, 159.65, 159.61, 154.82, 154.78, 152.92, 151.96, 151.86, 149.68, 148.89, 145.26, 145.00, 141.27, 140.25, 136.60, 131.30, 129.58, 129.47, 128.97, 126.77, 126.27, 124.04, 118.95, 112.70, 112.67, 112.53, 112.19, 109.77, 102.21, 102.19, 98.68, 69.62, 69.52, 69.07, 68.46, 45.70, 43.69, 41.71, 41.03; UV-VIS λ$_{max}$ 524 nm; Fluorescence λ$_{em}$ 537; MS-ESI (methanol) m/z 952.4 (M+1), 974.4 (M+23), 990.4 (M+39).

N-(1((Fluorescein-5-yl)amino)-1-thioxo-6,9,12-trioxa-2-azapentadecan-15-yl)-2-(4-(3-(2-(furan-2-yl)-8-methyl-8H-pyrazolo[4,3-e][1,2,4]triazolo[1,5-c]pyrimidin-5-yl)ureido)phenyl)acetamide (26). Yield 63%; orange solid; mp 143-149° C.; $^1$H-NMR (200 MHz, DMSO-d$_6$) δ 10.65 (bs, 1H), 10.36-9.87 (m, 3H), 9.51 (bs, 1H), 8.78 (s, 1H), 8.34-8.11 (m, 2H), 7.99 (s, 2H), 7.74 (d, J=8.2 Hz, 1H), 7.49 (d, J=7.8 Hz, 2H), 7.37-7.03 (m, 4H), 6.76 (s, 1H), 6.69-6.45 (m, 6H), 4.13 (s, 3H), 3.65-3.18 (m, 14H), 3.18-2.79 (m, 4H), 1.81 (bs, 2H), 1.63 (bs, 2H); $^{13}$C-NMR (50 MHz, DMSO-d$_6$) δ 180.23, 169.94, 168.39, 159.33, 159.27, 154.82, 151.74, 149.01, 148.96, 148.89, 145.34, 144.91, 141.28, 139.69, 136.40, 131.51, 129.47, 129.38, 129.27, 129.22, 128.92, 128.77, 126.34, 123.87, 118.94, 112.66, 112.49, 112.47, 112.39, 112.21, 112.15, 109.43, 102.16, 98.78, 69.72, 69.53, 69.51, 68.13, 68.01, 41.82, 41.35, 40.62, 35.97, 29.31, 28.58, 9.10; UV-VIS $\lambda_{max}$ 524 nm; Fluorescence $\lambda_{em}$ 537; MS-ESI (methanol) m/z 1046.4 (M+23).

General Synthesis for the N-(2-(furan-2-yl)-8-methyl-8H-pyrazolo[4,3-e][1,2,4]triazolo[1,5-c]pyrimidin-5-yl)alkynamides (36-39). Alkyne acid (1.1754 mmol) (19-22) was dissolved in deuterated chloroform (2 mL) and a catalytic amount of DMF was added (200 µL). The solution was cooled to 0° C. and oxalyl dichloride was added dropwise (1.1754 mmol, 99.5 µL) and the reaction was stirred at room temperature for 3 hours. A little amount of reaction was diluted in deuterated chloroform and monitored by $^1$H-NMR. The peaks of desired acyl chlorides (32-35) were shifted from those of the corresponding carboxylic acids. When the conversion was complete, to the reaction were added 1,4-dioxane (5 mL), triethylamine (1.959 mmol, 273 µL) and the 5-aminopyrazolo-triazolo-pyrimidine 27 (0.3918 mmol, 100 mg). The reaction was stirred at reflux overnight (TLC ethyl acetate 9.5/methanol 0.5) then the solvent was removed under vacuum. The residue was dissolved in water and extracted with dichloromethane (3 times), the organic layer was dried over sodium sulfate, and the solvent evaporated. The crude was purified on flash silica column chromatography (ethyl acetate 9.8/methanol 0.2) to give desired compound (36-39).

N-(2-(furan-2-yl)-8-methyl-8H-pyrazolo[4,3-e][1,2,4]triazolo[1,5-c]pyrimidin-5-yl)pent-4-ynamide (36). Yield 40%; pale brown solid; mp 264-271° C. d; $^1$H-NMR (200 MHz, CDCl$_3$) δ 9.11 (s, 1H), 8.22 (s, 1H), 7.65 (s, 1H), 7.23 (s, 1H), 6.61 (s, 1H), 4.20 (s, 3H), 3.50 (t, J=6.8 Hz, 2H), 2.70 (t, J=6.8 Hz, 2H), 2.01 (s, 2H); $^{13}$C-NMR (50 MHz, CDCl$_3$) δ 171.47, 155.68, 153.84, 148.92, 145.09, 144.81, 138.67, 125.55, 111.13, 112.24, 100.04, 82.89, 74.39, 69.33, 41.06, 37.05, 13.86. MS-ESI (methanol) m/z 336.2 (M+1), 358.1 (M+23), 374.1 (M+39).

N-(2-(furan-2-yl)-8-methyl-8H-pyrazolo[4,3-e][1,2,4]triazolo[1,5-c]pyrimidin-5-yl)hex-5-ynamide (37). Yield 19%; pale yellow solid; mp 210-216° C. d; $^1$H-NMR (200 MHz, CDCl$_3$) δ 9.05 (s, 1H), 8.21 (s, 1H), 7.65 (s, 1H), 7.26 (s, 1H), 6.62 (s, 1H), 4.21 (s, 3H), 3.26 (t, J=6.3 Hz, 2H), 2.40 (s, 2H), 2.18-1.85 (m, 3H); $^{13}$C-NMR (50 MHz, CDCl$_3$) δ 172.67, 156.07, 153.55, 149.05, 145.19, 144.92, 138.68, 124.95, 112.92, 112.16, 100.13, 83.49, 69.33, 40.80, 36.69, 23.34, 18.04. MS-ESI (methanol) m/z 372.2 (M+23).

N-(2-(furan-2-yl)-8-methyl-8H-pyrazolo[4,3-e][1,2,4]triazolo[1,5-c]pyrimidin-5-yl)hept-6-ynamide (38). Yield 15%; white solid; mp 208-215° C. d; $^1$H-NMR (200 MHz, CDCl$_3$) δ 9.02 (s, 1H), 8.21 (s, 1H), 7.65 (s, 1H), 7.23 (d, J=3.2 Hz, 1H), 6.60 (d, J=3.2 Hz 1H), 4.20 (s, 3H), 3.36 (t, J=7 Hz, 2H), 2.32-2.24 (m, 2H), 1.97-1.86 (m, 3H), 1.77-1.66 (m, 2H); $^{13}$C-NMR (50 MHz, CDCl$_3$) δ 173.09, 155.76, 153.92, 148.96, 144.96, 138.75, 125.38, 112.89, 112.19, 100.05, 84.24, 68.76, 41.03, 37.23, 28.01, 23.52, 18.56. MS-ESI (methanol) m/z 364.2 (M+1), 386.2 (M+23), 402.1 (M+39).

N-(2-(furan-2-yl)-8-methyl-8H-pyrazolo[4,3-e][1,2,4]triazolo[1,5-c]pyrimidin-5-yl)oct-7-ynamide (39). Yield 40%; white solid; mp 204-208° C. d; $^1$H-NMR (200 MHz, CDCl$_3$) δ 8.99 (s, 1H), 8.21 (s, 1H), 7.65 (d, J=1.8 Hz, 1H), 7.25 (d, J=3.2 Hz, 1H), 6.61 (dd, J=1.8 Hz, J=3.2 Hz 1H), 4.20 (s, 3H), 3.24 (t, J=7.2 Hz, 2H), 2.23-2.04 (m, 2H), 1.95-1.73 (m, 3H), 1.61-1.56 (m, 4H); $^{13}$C-NMR (50 MHz, CDCl$_3$) δ 173.28, 155.74, 153.95, 148.95, 144.96, 138.76, 125.37, 112.88, 112.18, 100.06, 84.57, 68.4, 41.02, 37.62, 28.47, 28.38, 23.91, 18.48. MS-ESI (methanol) m/z 378.2 (M+1), 400.2 (M+23), 416.1 (M+39).

EXAMPLE 2

This example illustrates some of the biological properties of compounds in accordance with embodiments of the invention.

Cell Cultures and Membrane Preparation

Chinese hamster ovary (CHO) cells without heterologous AR expression were grown in DMEM/F12 (1:1) medium with 10% FBS, 2 mM L-glutamine, 50 U/ml penicillin/streptomycin. CHO cells expressing the $A_1$ or $A_3$ AR and HEK293 cells expressing the $A_{2A}$ AR were grown in the same medium but in the presence of 500 µg/ml hygromycin B and 800 µg/ml of G418, respectively. Cells, used for FCM analysis, were grown in 6-well plates (approximately 400,000 cells/well) and incubated at 37° C. for 24 h in the presence of 5% $CO_2$. When confluency of the cells was reached 80% (approximately $10^6$ cells/well), medium was replaced with fresh medium and MRS5449 was added in the presence or absence of competitive antagonists, and cells were processed for FCM.

For cell cultures used in radioligand binding assays, after harvest and homogenization, the cells were centrifuged at 200×g for 10 min, and the pellet was re-suspended in 50 mM Tris-HCl buffer (pH 7.5), containing 10 mM $MgCl_2$. The suspension was homogenized with an electric homogenizer for 10 s and was then re-centrifuged at 20,000×g for 20 min at 4° C. The resultant membrane pellets were resuspended in buffer in the presence of 3 units/ml adenosine deaminase, and the suspension was stored at −80° C. until the binding experiments. The protein concentration was measured using the Bradford assay [21]. Radioligand membrane binding assays Radioligand binding assays at $hA_1$, $hA_{2A}$, and $hA_3$ARs were performed according to the procedures described in Gao, Z. G., et al., *Biochem Pharmacol.* 2003; 65: 1675-84, using the radiolabeled agonists [$^3$H]R-PIA from Moravek Biochemicals (Brea, Calif.) or [$^3$H]CGS21680 and [$^{125}$I]I-AB-MECA from PerkinElmer (Waltham, Mass.) for the $hA_1$, $hA_{2A}$AR, and $hA_3$AR assays, respectively.

Cyclic AMP Accumulation Assay

CHO cells stably expressing the $hA_3$AR were seeded in 24-well plates and incubated at 37° C. overnight. The medium was removed the following day and replaced with DMEM containing 50 mM HEPES, 10 µM rolipram, 3 units/ml adenosine deaminase (Worthington Biochemical Corp., Lakewood, N.J.), and increasing concentrations of agonists and incubated for 30 mM. Forskolin (10 µM) was added and incubated for an additional 15 min. The medium was removed, and the cells were lysed with 200 µL of 0.1 M HCl. 100 µl of the HCl solution was used in the Sigma Direct cAMP Enzyme Immunoassay following the instructions provided with the kit. The OD values were measured with a SpectraMax M5 Microplate reader (Molecular Devices, Sunnyvale, Calif.) at 405 nm.

Fluorescence Microscopy Experiments

CHO cells stably expressing the $hA_3$AR were grown on sterile coverslips in 6-well plates, and experiments were performed when the cells reach 70% confluency after refreshing the medium. The cells were incubated with 50 nM MRS5449 for different time intervals from 15 min to 3 h at 37° C. in an atmosphere containing 5% CO2. At the end of each time interval, the medium was removed, and cells were washed three times with ice-cold PBS (Crystalgen, Commack, N.Y.). The coverslips containing the cells were placed on sterile slides, and the cells were observed under a Zeiss AxioCam MRm fluorescence microscope (Carl Zeiss, Inc., Thornwood, N.Y.).

Fluorescent Ligand Binding in Intact Cho Cells Expressing the $A_3AR$

In preliminary binding experiments of compounds 1-6 and MRS5449 were incubated with CHO cells expressing the $hA_3AR$ for 1 h at 37° C. in an atmosphere containing 5% $CO_2$. The concentrations used were incubated with 1.5 µM 1, 5 µM 2, 1.5 µM 3, 10 µM 4, 20 µM 5, 15 µM 6, or 10 nM MRS5449. For further binding experiments with MRS5449, control CHO cells (CHO cells without heterologous receptor expression) and CHO cells expressing $hA_3AR$ were incubated with 10 nM MRS5449 for 3 h.

In saturation binding experiments, CHO cells expressing the hA3AR were incubated with concentrations of MRS5449 ranging from 2.5 nM to 250 nM for 1 h. To study binding kinetics of MRS5449, CHO cells expressing the $hA_3AR$ were incubated with 10 nM MRS5449 for different time intervals from 5 min to 3 h. The association and dissociation rate was measured as follows: 10 nM MRS5449 was added to CHO cells expressing the $A_3AR$ and measured total binding at different time intervals. After 90 min, dissociation was initiated by adding 10 µM of non-fluorescent $A_3AR$ antagonist MRS1220 and then measured the dissociation at different time intervals.

To determine binding affinities of known AR ligands using MRS5449 as a tracer, $hA_3AR$-expressing CHO cells were incubated with different concentrations of ligands in the presence of 5 nM MRS5449 for 90 min. Total binding was measured in the absence of the competitor. Nonspecific binding was determined in the presence of 10 µM MRS1220.

At the end of each time interval, the medium was removed and cells were washed three times with ice-cold DPBS. After washing, 1 ml 0.2% EDTA solution was added to each well, and cells were incubated at 37° C. for 7 min. Following cell detachment, 1 ml medium was added to each well to neutralize the EDTA. The cell suspensions were transferred to polystyrene round-bottom BD Falcon tubes (BD, Franklin Lakes, N.J.) and centrifuged for 5 min at 23° C. and 400×g. After centrifugation, the supernatant was discarded, and cells were washed with 3 ml PBS and centrifuged again at 23° C. and 400×g for 5 min. After discarding the supernatant, cells were suspended in 0.5 ml PBS and analyzed by FCM.

FCM Calibration

A measurable intrinsic parameter of a fluorescent ligand or particle is its fluorescence yield, which can be expressed as molecular equivalent values of free fluorophore in solution (MESF). Standard particles suspensions with assigned MESF values, e.g. Quantum Alexa Fluor-488 MESF beads (Bangs Laboratories, Inc., Fishers, Ind.), establish an instrument-independent scale that accurately depicts the molar quantity of fluorophores on labeled particles.

The mean fluorescence intensity (MFI) values of the standard particles were recorded under optimized instrument setting and converted into MESF values using the QuickCal program v. 2.3 (Bangs Laboratories, Inc., Fishers, Ind.). MFIs of receptor-bound fluorescent small molecules in this study were measured under exactly the same conditions and the assigned MESF values were extrapolated from the calibration curve.

FCM Analysis

The intensity of fluorescence emission of each sample was measured by using FCM. Cell suspensions were vortexed briefly before analysis on a Becton and Dickinson FACSCalibur flow cytometer (BD, Franklin Lakes, N.J.) with excitation at 488 nm. Samples were maintained in the dark during the analysis to avoid photobleaching. MFIs were obtained in the FL-1 channel in log mode. Ten thousand events were analyzed per sample. Data were collected using Cell Quest Pro software (BD, Franklin Lakes, N.J.) and analyzed by Cyflogic v. 1.2.1 software (CyFlo, Ltd., Turku, Finland).

Data Analysis

Data analysis was performed with the Prism 5 (GraphPad, San Diego Calif.) software. The mean autofluorescence of CHO cells was measured in the absence of the fluorescent ligand. The mean fluorescence in the presence of fluorescent ligand was corrected by subtracting this value; Wood, J C S, *Curr Protoc Cytom* 2009; 1.4.1-1.4.14.

Pharmacological and Spectral Characterization of AR Antagonist Ligands

Figure 1:
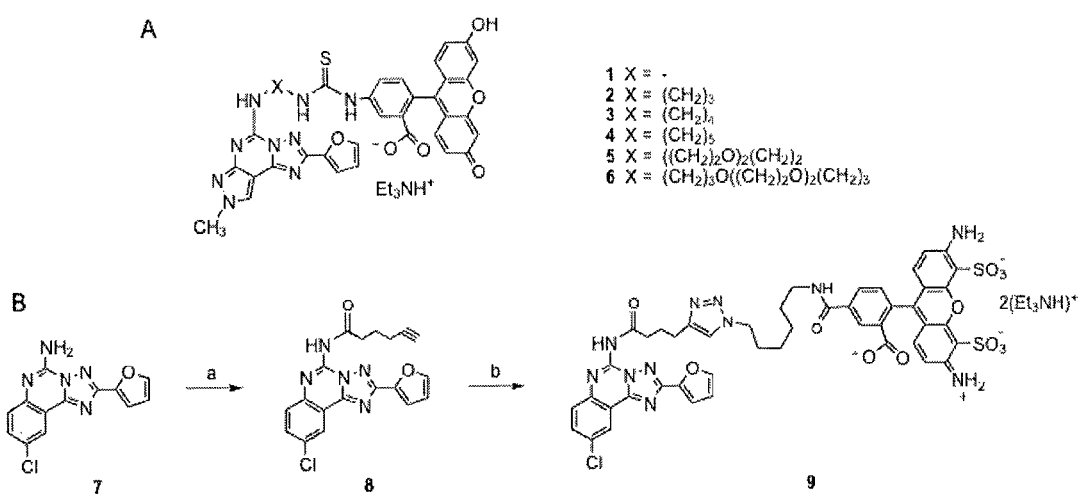
Figure 2A:
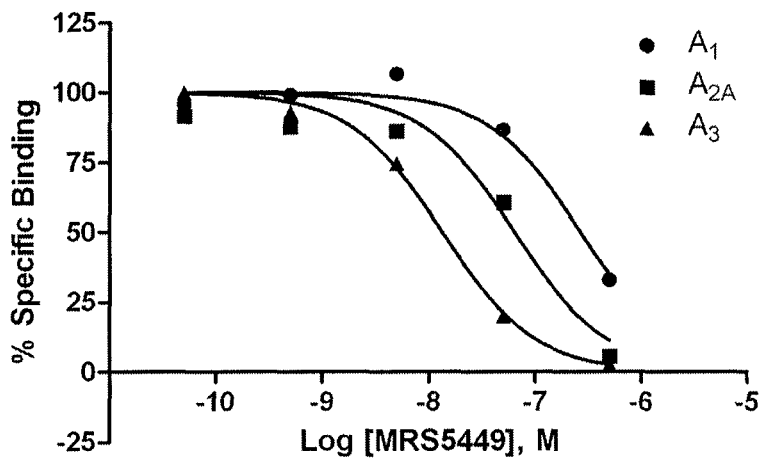

The binding affinity of these derivatives at three subtypes of hARs was determined using standard radioligand binding methods, and the $K_i$ values are shown in Table 1. The binding affinities of the conjugates 1-6 show that roughly µM affinity was not exceeded at three AR subtypes. The most potent $hA_3AR$ ligands in the group of PTP derivatives were 1 and 3 with $K_i$ values of 780 and 720 nM, respectively, in a binding assay using [$^{125}$I]I-AB-MECA as a radioligand. The $hA_3AR$ binding of TQ derivative MRS5449 displayed a $K_i$ value of 6.4 nM (FIG. 2A). The affinity of MRS5449 at two other ARs was lower; at $hA_1$ and $hA_{2A}ARs$, the $K_i$ values in inhibition of radioligand binding were 87 nM and 73 nM, respectively. Thus, the selectivity for the $A_3AR$ was over 10-fold. The effect of chain extension at the exocyclic amine of 7, as found in 8 or when terminated in a click-conjugated fluorophore in MRS5449, was to greatly reduce $hA_1$ and $hA_{2A}AR$ affinity while maintaining nearly identical $A_3AR$ affinity. Moreover the conjugation of the fluorophore increased the $hA_3AR$ affinity.

Figure 2B:
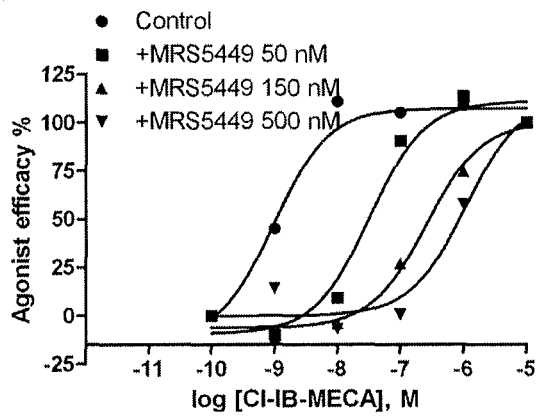
Figure 2C:
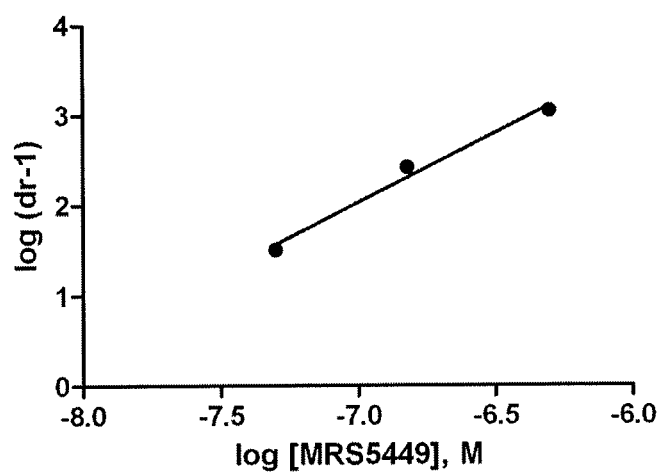

In a functional assay of cyclic AMP accumulation in CHO cells expressing the $A_3AR$, MRS5449 concentration-dependently antagonized the effects of $A_3AR$ agonist Cl-IB-MECA (FIG. 2B) corresponding to a $K_B$ value of 4.8 nM (FIG. 2C). MRS5449 displayed excitation and emission peaks at 494 and 523 nm, respectively.

Figure 3:
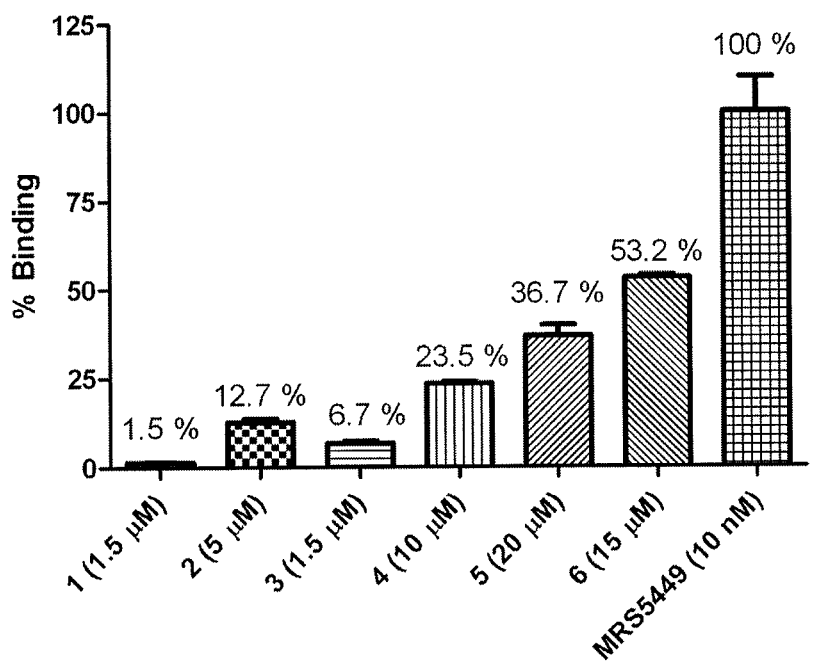

In preliminary FCM experiments, the binding affinity of compounds 1-6 and MRS5449 at the $hA_3AR$ expressed on CHO cells was measured by recording MFI values of the cell-fluorescence in the presence of small molecule conjugates and converting them into MESF values. However, conjugates 1-6 resulted in very low fluorescence emission, and only MRS5449 produced a sufficiently high MFI for further investigations in fluorescent experiments, even at 250 to 1000-fold lower concentration than compounds 1-6 (FIG. 3). Compared with the binding to the $A_3AR$ (expressed as 100%), the respective binding of MRS5449 to CHO cells expressing the $A_1AR$ and HEK cells expressing the $A_{2A}AR$ was only 0.3% and 0.5%.

According to its fluorescent properties, binding affinity and selectivity at the $hA_3AR$, MRS5449 is a preferred ligand for further examination as a fluorescent tracer in various assay modes.

Figure 4:
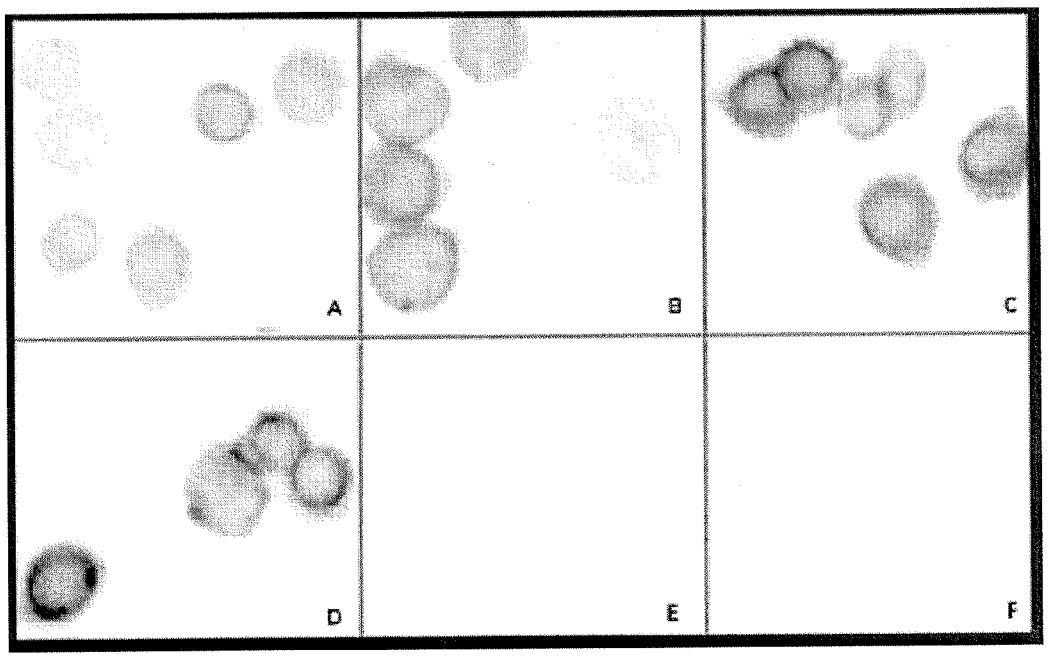

Fluorescence micrographs showing the binding of 50 nM MRS5449 to the $A_3AR$ expressed in CHO cells at different time points are shown in FIG. 4. The fluorescence was highly associated with the plasma membrane, and internalized MRS5449 did not appear to be the source of most of the fluorescence. The corresponding control experiments, performed either in the absence of MRS5449 or in its presence except with preincubation with $hA_3AR$ antagonist MRS1220 (10 µM), did not indicate any appreciable bound fluorescence. The intensity of fluorescence gradually increased over an incubation period of 15 min-180 min.

FCM Calibration

The fluorescence intensities of AlexaFluor-488 labeled standard beads were analyzed with assigned MESF values at five different fluorescence intensity levels. This was used to establish a calibration curve to relate relative fluorescence signals to absolute fluorescence that was translated to molar concentration of the fluorophore. By converting MFI values into MESF values based on this calibration curve, molar quantitation was accomplished.

Fluorescent Ligand Binding Experiments

Figure 5A:
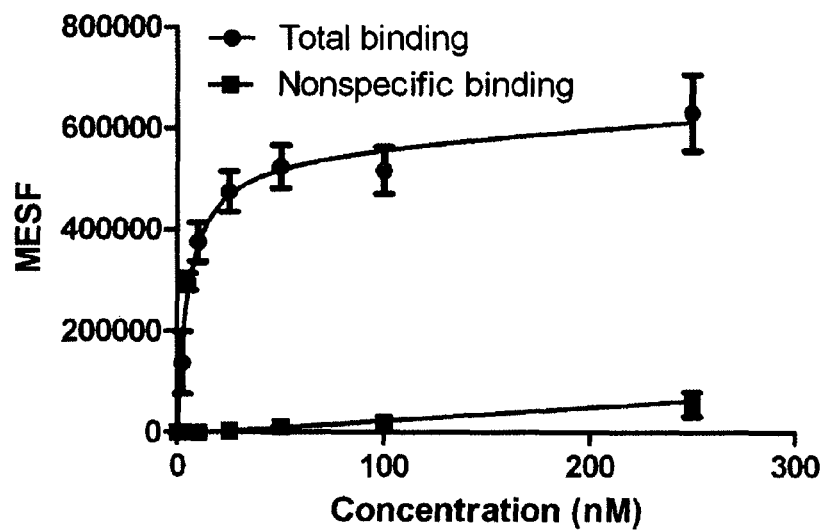
Figure 5B:
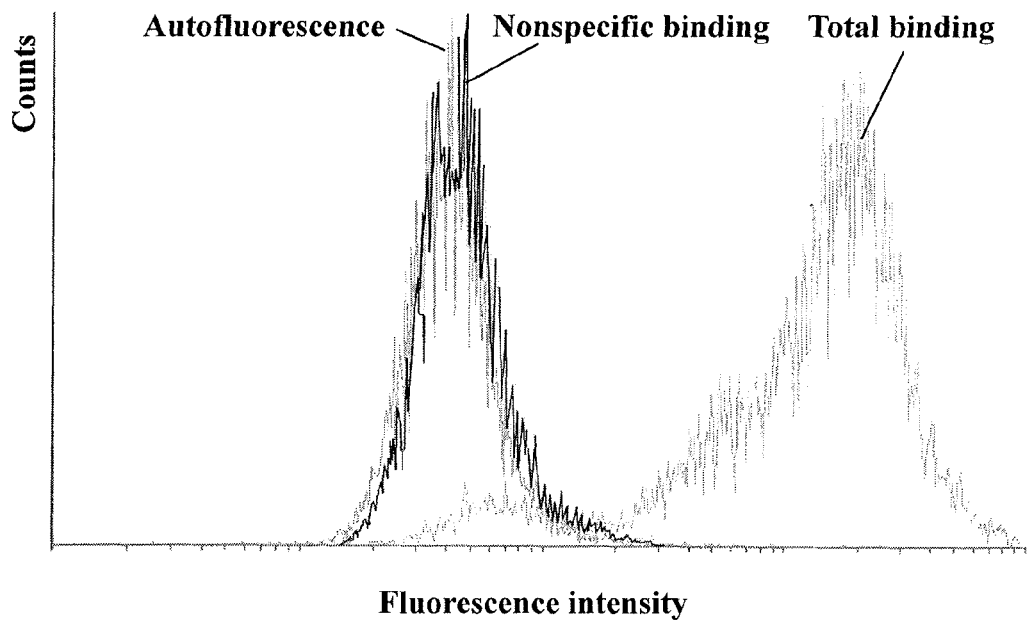

In a saturation binding experiment, the concentration of fluorescent ligand MRS5449 was varied from 2.5 nM to 250 nM and MFI of the receptor bound ligand was measured. A saturation binding curve was obtained using MESF values, since FCM is insensitive to unbound soluble ligand (FIG. 5A). As a negative control CHO cells expressing hA$_3$AR were used in the absence of fluorescence ligand (autofluorescence). Nonspecific binding of 10 nM MRS5449 measured in the presence of 10 μM antagonist MRS1220 or 10 μM agonist Cl-IB-MECA or in control CHO cells (without heterologous receptor expression) was less than 1% of total binding. A FCM histogram of the total binding and nonspecific binding to hA$_3$AR expressing CHO cells using MRS5449 at the suitable tracer concentration of 10 nM is shown in FIG. 5B. Total binding was significantly higher than the nonspecific binding in antagonist-treated cells, which was similar to the autofluorescence of the cells. The peak of the total binding located within the optimal window for analysis and was well separated from the levels of nonspecific binding and the autofluorescence. From the saturation curve, the equilibrium binding constant ($K_d$) was determined to be 5.15±1.11 nM, which is similar to a $K_i$ value of 6.4 nM obtained from radioligand binding experiments.

Figure 5C:
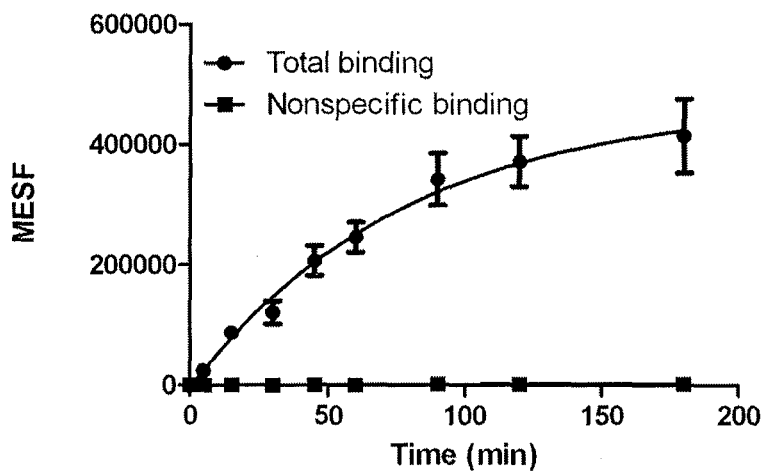

The association kinetics of the fluorescent ligand MRS5449 was determined using an FCM assay. FIG. 5C shows the time-dependent binding of 10 nM MRS5449 to the hA$_3$AR. The $t_{1/2}$ for association was found to be 53 min.

Figure 5D:
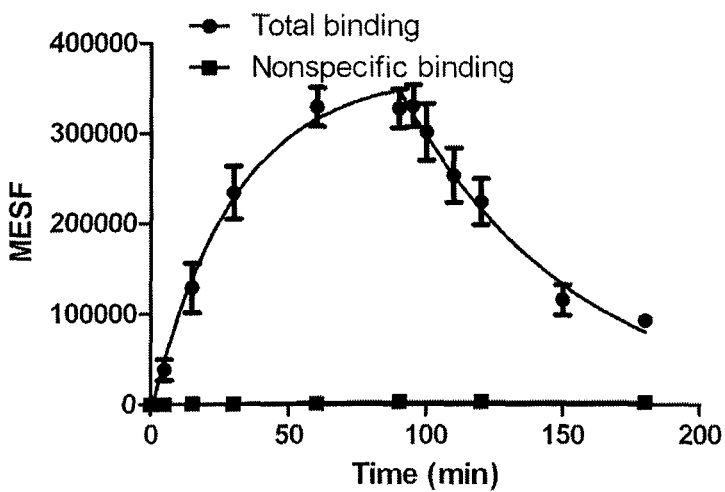
Figure 6:
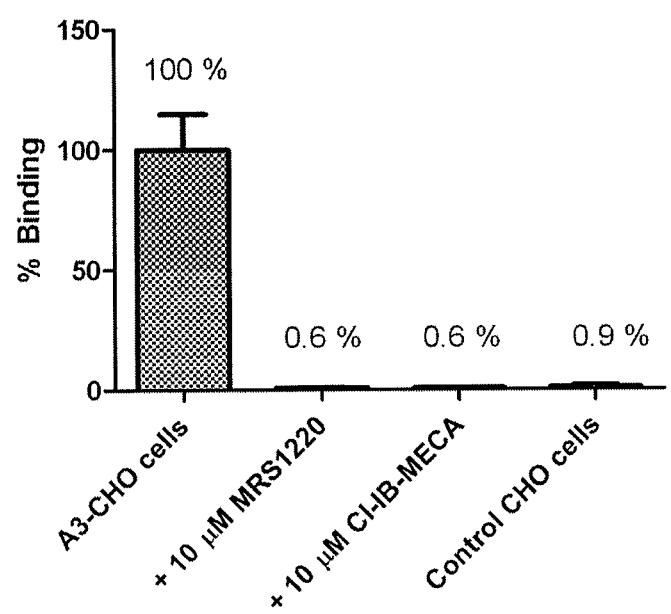

Dissociation was determined by adding 10 μM MRS1220 after equilibrium was reached (FIG. 5D). The $K_d$ value determined through association and dissociation kinetic experiments is 6.65±0.55 nM, which correlated well with the equilibrium binding constant determined in a saturation binding experiment and also closely matched the $K_i$ value in radioligand binding assays.

Screening of Known AR Ligands Using MRS5449 as a Tracer

Figure 7A:
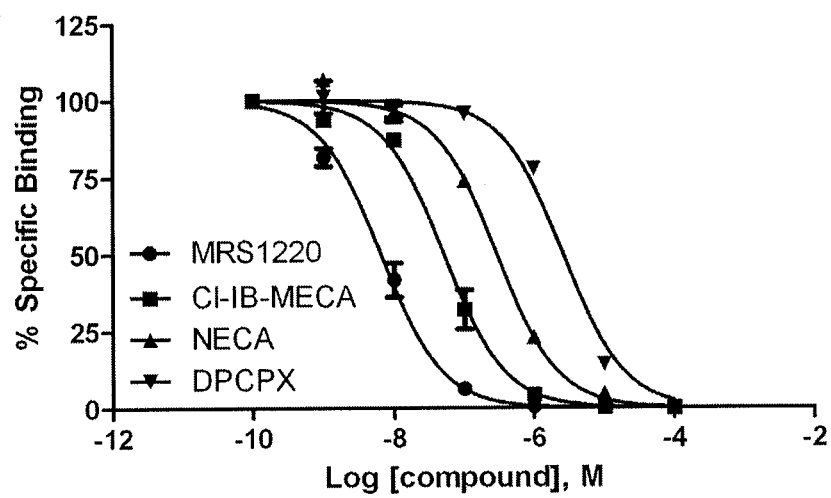
Figure 7B:
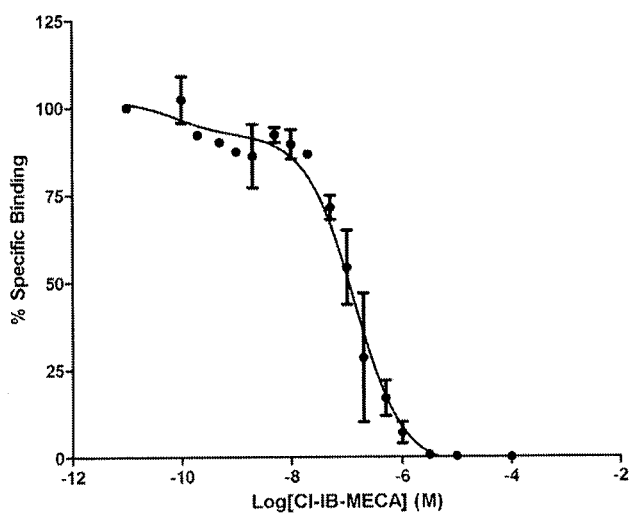
Figure 8:
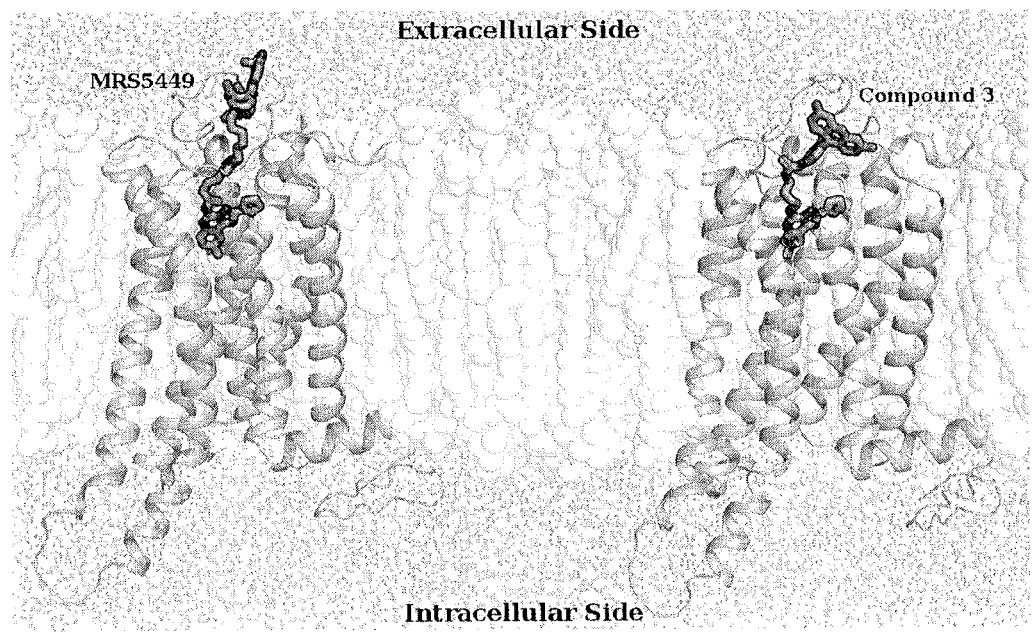
FIG. 8 depicts the hypothetical binding conformations at the $hA_3AR$ model of compound 9 (on the left) and compound 3 (on the right), obtained after molecular modeling studies. Ligand-receptor models are embedded in a solvated lipid bilayer, simulating the cell membrane, and are viewed through a cross-section of the plasma membrane.
Figure 9:
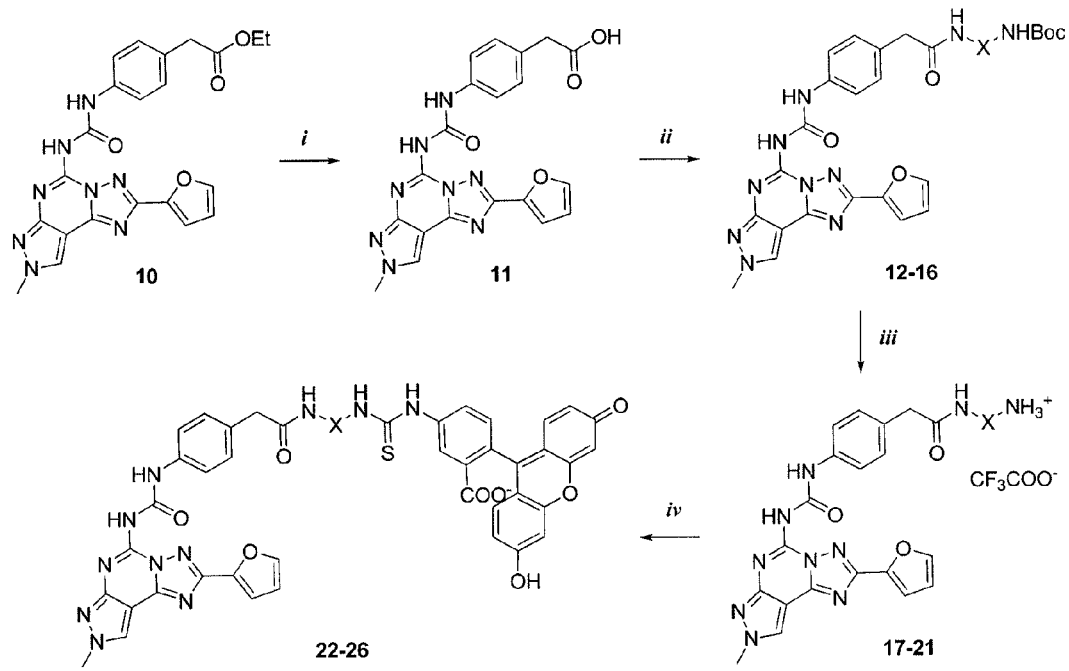
FIG. 9 depicts a reaction scheme to prepare compounds 22-26 in accordance with an embodiment of the invention.
Figure 10:
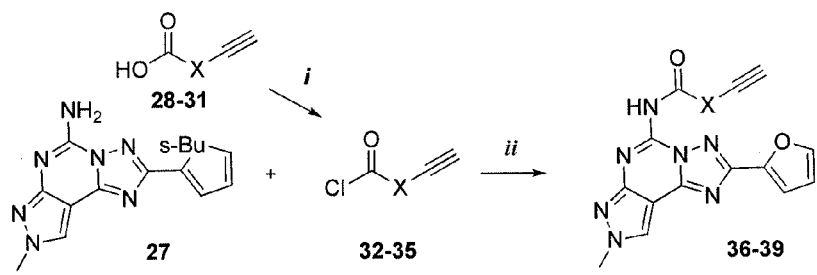
FIG. 10 depicts a reaction scheme to prepare compounds 36-39 in accordance with an embodiment of the invention.
Figure 11:
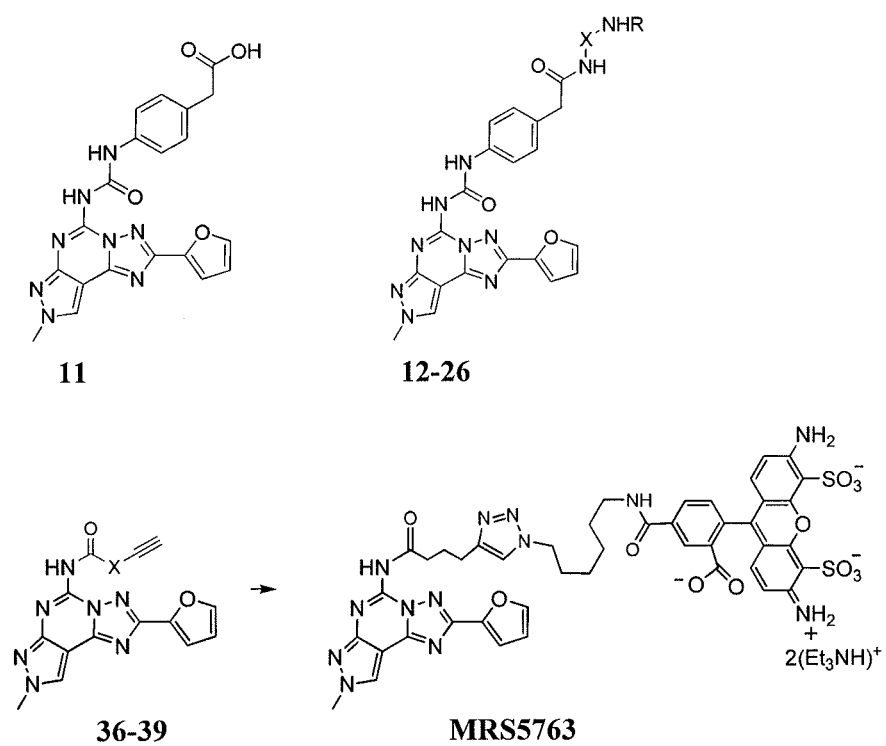
FIG. 11 depicts the structures of compounds 11-26 and 36-39 and MRS5763 in accordance with an embodiment of the invention.
Figure 12:
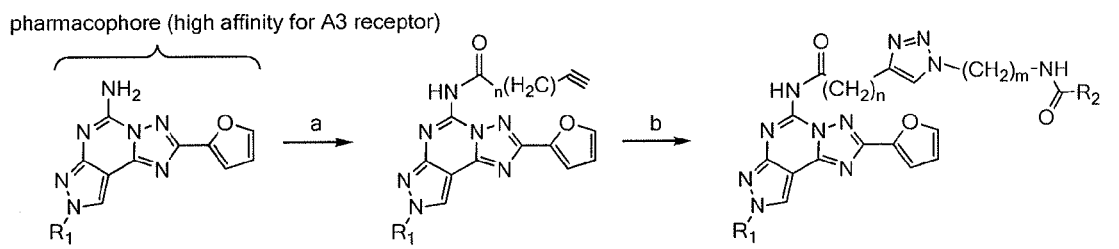
FIG. 12 depicts compounds in accordance with an embodiment of the invention.
Figure 13:
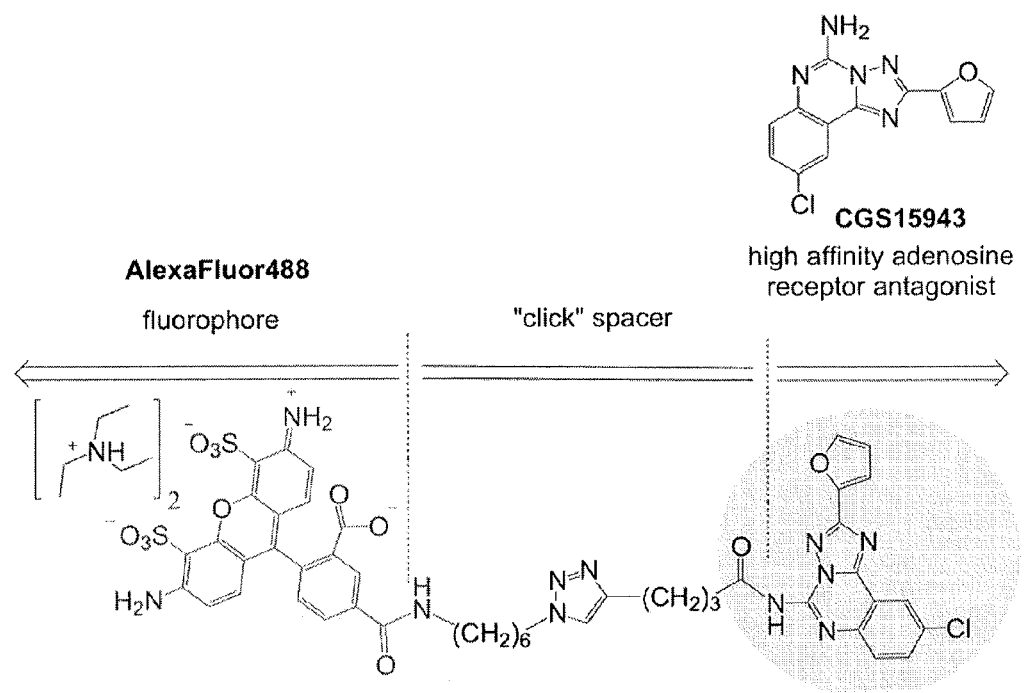
FIG. 13 depicts compounds in accordance with another embodiment of the invention.

Competition for fluorescent binding with known AR ligands was performed using FCM. To determine the $K_i$ values of known ligands, MRS5449 was used as a tracer, at a concentration of 5 nM (close to its $K_d$ value). Competitive binding results with known agonists and chemically diverse antagonists are shown in FIG. 7A and Table 2. The observed pharmacology of antagonists in this whole cell FCM assay corresponded to that previously observed for the hA$_3$AR. However, $K_i$ values of known AR agonists in inhibition of MRS5449 binding were roughly 5-20 fold weaker than in agonist radioligand binding experiments in membranes. A further detailed examination of the displacement curve of Cl-IB-MECA for the antagonist fluorescent ligand MRS5449 suggests that multiple agonist binding states of the hA$_3$AR can be demonstrated (FIG. 7B). Analysis the binding curve with a two-site binding model shows that Cl-IB-MECA binds to a high-affinity binding component corresponding to a $K_i$ value 0.1 nM, i.e. closer to the $K_i$ value determined using an agonist radioligand. A low affinity binding component for Cl-IB-MECA was determined to correspond to a $K_i$ value of 136 nM (FIG. 7B).

TABLE 1

Binding affinity of a series of fluorescent AR antagonist derivatives at three subtypes of hARs.[a]

| Compound | A$_1$ $K_i$ (nM) or % Inhibition | A$_{2A}$ $K_i$ (nM) or % Inhibition | A$_3$ $K_i$ (nM) or % Inhibition |
|---|---|---|---|
| 1 | 9500[b] | 920 ± 110 | 780[b] |
| 2 | (5 ± 2%) | 2480 ± 420 | 2390 ± 660 |
| 3 | (7 ± 5%) | 460 ± 60 | 720 ± 70 |
| 4 | (9 ± 5%) | 1750 ± 470 | 5660 ± 610 |
| 5 | (0%) | (30 ± 6%) | 9390 ± 1730 |
| 6 | (0%) | 6010 ± 420 | 7090 ± 370 |
| 7 | 3.5 | 1.2 | 35 |
| 8 | 170 ± 40 | 51.0 ± 10.0 | 33.5 ± 10.1 |
| 9[c] | 87.0 ± 24.0 | 73.0 ± 8.0 | 6.4 ± 2.5 |

[a]All experiments were done on CHO (A$_1$ and A$_3$ARs) or HEK293 (A$_{2A}$AR) cells stably expressing one of three subtypes of hARs. The binding affinity for A$_1$, A$_{2A}$ and A$_3$ARs was expressed as $K_i$ values (n = 3-5, unless noted) and was determined by using agonist radioligands ([$^3$H]R-PIA; [$^3$H]CGS21680; or [$^{125}$I]-AB-MECA; respectively), unless noted. A percent in parentheses refers to inhibition of radioligand binding at 10 μM unless noted. Binding data for CGS15943 7 were taken from literature reports; Fredholm, B. B., et al., supra. IC$_{50}$ values were converted to $K_i$ values as reported; Gessi, S. et al., Clin Cancer Res 2004; 10:5895-901.
[b]duplicate determination.
[c]9, MRS5449.

TABLE 2

Inhibition of A$_3$AR binding of known AR agonists and antagonists using MRS5449 as a FCM tracer in whole cells.

| Compound (selectivity) | hA$_3$AR radioligand binding, $K_i$ (nM)[a] | FCM binding at hA$_3$AR, $K_i$ (nM) |
|---|---|---|
| Agonists | | |
| CPA | 72 | 1490 ± 230 |
| CGS21680 | 67 | 1580 ± 190 |
| Cl-IB-MECA | 1.4 | 27.7 ± 6.3 |
| IB-MECA | 1.8 | 10.9 ± 1.9 |
| NECA | 25 | 149 ± 13 |
| Antagonists | | |
| DPCPX | 3980 | 1320 ± 60 |
| ZM241385 | 743 | 300 ± 27 |
| MRS1220 | 0.65 | 3.46 ± 0.8 |
| PSB-10[b] | 0.441 | 9.54 ± 2.2 |
| XAC | 13.8 | 19.9 ± 1.8 |
| CGS15943 | 35 | 16.1 ± 6.2 |
| Theophylline | 22,300 | 29,400 ± 1400 |

[a]$K_i$ values for A$_3$AR binding affinity in cell membrane preparations using [$^{125}$I]-AB-MECA are reported [Fredholm, B. B., et al., supra., Kim, Y. C., et al., J Med Chem 1996; 39: 4142-8, Muller, C., et al., Biomembranes 2011, 1808: 1290-308].
[b]The potency of PSB-10 was 4 nM in a functional assay.

TABLE 3

| Cmpd | X | R | A$_1$ % inhibition or $K_i$ (nM) | A$_{2A}$ % inhibition or $K_i$ (nM) | A$_3$ % inhibition or $K_i$ (nM) |
|---|---|---|---|---|---|
| 11 EA2/MRS5811 | — | — | 4% ± 3% | 1,010 ± 160 | 128 ± 26 |
| 12 EA12/MRS5821 | (CH$_2$)$_3$ | Boc | 15% ± 5% | 150 ± 11 | 2.75 ± 0.20 |
| 13 EA15/MRS5824 | (CH$_2$)$_4$ | Boc | 2% ± 2% | 304 ± 20 | 3.46 ± 0.33 |
| 14 EA6/MRS5815 | (CH$_2$)$_5$ | Boc | 14% ± 3% | 376 ± 96 | 4.47 ± 1.06 |
| 15 EA3/MRS5812 | (CH$_2$CH$_2$O)$_2$CH$_2$CH$_2$ | Boc | 7% ± 5% | 456 ± 96 | 74.8 ± 10.1 |

TABLE 3-continued

| Cmpd | X | R | $A_1$ % inhibition or $K_i$ (nM) | $A_{2A}$ % inhibition or $K_i$ (nM) | $A_3$ % inhibition or $K_i$ (nM) |
|---|---|---|---|---|---|
| 16 EA9/MRS5818 | $(CH_2)_3O(CH_2CH_2O)_2(CH_2)_3$ | Boc | 11% ± 5% | 327 ± 32 | 82.4 ± 20.1 |
| 17 EA13/MRS5822 | $(CH_2)_3$ | H | 9% ± 3% | 175 ± 27 | 8.06 ± 2.47 |
| 18 EA16/MRS5825 | $(CH_2)_4$ | H | 4% ± 1% | 172 ± 33 | 6.00 ± 1.29 |
| 19 EA7/MRS5816 | $(CH_2)_5$ | H | 6% ± 4% | 203 ± 52 | 2.66 ± 0.48 |
| 20 EA4/MRS5813 | $(CH_2CH_2O)_2CH_2CH_2$ | H | 17% ± 3% | 267 ± 61 | 19.2 ± 3.3 |
| 21 EA10/MRS5819 | $(CH_2)_3O(CH_2CH_2O)_2(CH_2)_3$ | H | 1% ± 1% | 328 ± 77 | 10.3 ± 0.4 |
| 22 EA14/MRS5823 | $(CH_2)_3$ | FITC | 27% ± 1% | 110 ± 18 | 104 ± 44 |
| 23 EA17/MRS5826 | $(CH_2)_4$ | FITC | 28% ± 8% | 60.4 ± 6.2 | 73.6 ± 14.7 |
| 24 EA8/MRS5817 | $(CH_2)_5$ | FITC | 21% ± 5% | 106 ± 14 | 96.7 ± 26.9 |
| 25 EA5/MRS5814 | $(CH_2CH_2O)_2CH_2CH_2$ | FITC | 29% ± 1% | 95.7 ± 25.4 | 137 ± 28 |
| 26 EA11/MRS5820 | $(CH_2)_3O(CH_2CH_2O)_2(CH_2)_3$ | FITC | 32% ± 6% | 91.5 ± 20.0 | 207 ± 95 |
| 36 EA19 (5-pent-4-ynamide) MRS5839 | $(CH_2)_2$ | — | 55% ± 4% | 133 ± 37 | 11.0 ± 0.6 |
| 37 MRS5846/5762 5-hex-5-ynamide | $(CH_2)_3$ | — | To be measured | 199 (n = 1) | 4.11 ± 0.93 |
| 38 EA18 (5-hept-6-ynamide) MRS5838 | $(CH_2)_4$ | — | 891 ± 265 | 151 ± 33 | 7.26 ± 1.04 |
| 39 EA20 (5-oct-7-ynamide) MRS5840 | $(CH_2)_5$ | — | 62% ± 3% | 482 ± 141 | 12.8 |
| MRS5763 | — | — | — | 90 | 31.8 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

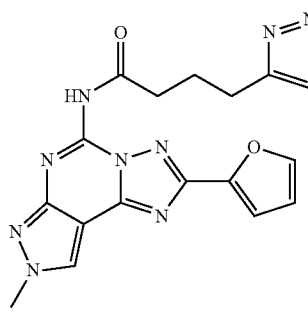
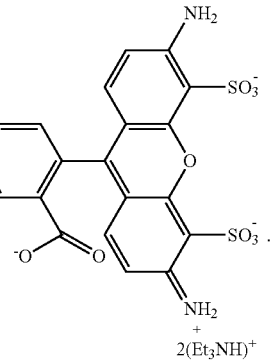

12. A diagnostic composition comprising a compound or salt of claim 1 and a pharmaceutically acceptable carrier.
13. The compound or salt of claim 1, which is:
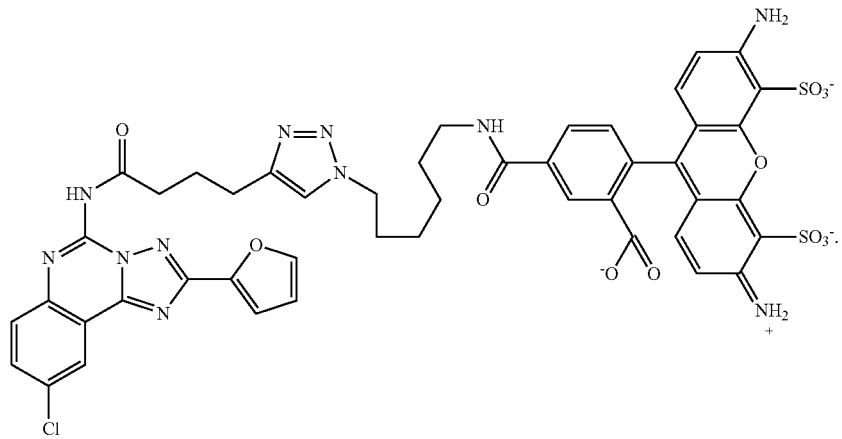

The invention claimed is:

1. A compound of the formula (I):

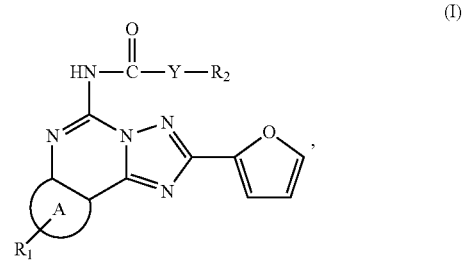

(I)

wherein:

A, together with $R_1$, is

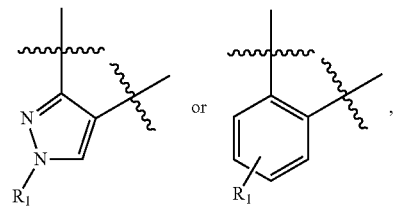

or

Y is

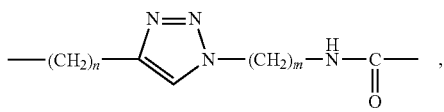

R₁ is FLUORO, BROMO, IODO, C1-C3 alkyl, halo C1-C6 alkyl, cyano C1-C6 alkyl, nitro C1-C6 alkyl, or benzyl, wherein the benzyl is optionally substituted with alkyl, halo, cyano, or nitro;

R₂ is a fluorophore moiety selected from the group consisting of FITC, NBD, Dansyl, Squaraine Rotaxane, Bodipy FL, Bodipy TR, Bodipy-630/650, Texas Red, Cy5, 1-pyrene, EVOBlue 30, Alexa Fluor 532, Alexa Fluor 488-5, 488-6, or mixture thereof, Tamra, Tamra 5/6-X-SE, Alexa Fluor 488 azide 5 isomer, NIR dye 700, and NIR dye 800;

n, m, and p are independently 1 to 6;

or a pharmaceutically acceptable salt thereof.

2. The compound or salt of claim 1, which is a compound of formula (Ia) or (Ib):

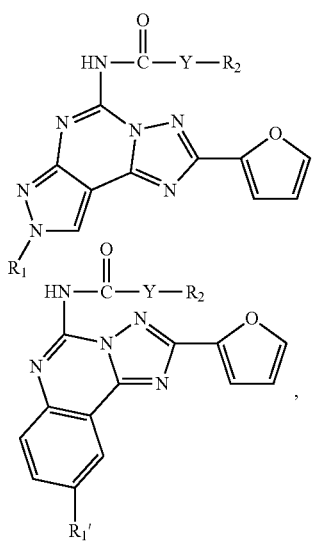

wherein R₁ is C1-C3 alkyl, and R₁' is C1-C6 alkyl, halo C1-C6 alkyl, cyano C1-C6 alkyl, nitro C1-C6 alkyl, or benzyl, wherein the benzyl is optionally substituted with alkyl, halo, cyano, or nitro.

3. The compound or salt of claim 1, which is of formula (IIa) or (IIb):

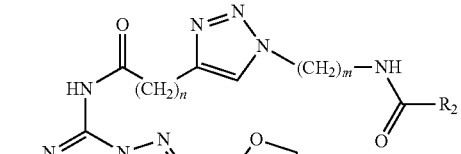

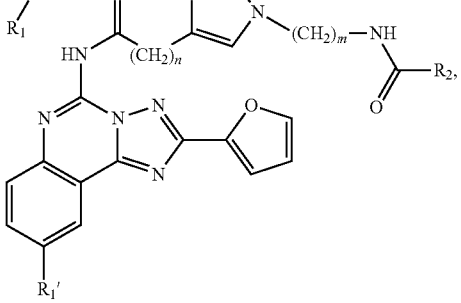

wherein R₁ and R₁' are independently C1-C3 alkyl, halo C1-C6 alkyl, cyano C1-C6 alkyl, nitro C1-C6 alkyl, or benzyl, wherein the benzyl is optionally substituted with alkyl, halo, cyano, or nitro;

R₂ is a fluorophore moiety selected from the group consisting of FITC, NBD, Dansyl, Squaraine Rotaxane, Bodipy FL, Bodipy TR, Bodipy-630/650, Texas Red, Cy5, 1-pyrene, EVOBlue 30, Alexa Fluor 532, Alexa Fluor 488-5, 488-6, or mixture thereof, Tamra, Tamra 5/6-X-SE, Alexa Fluor 488 azide 5 isomer, NIR dye 700, and NIR dye 800.

4. The compound or salt of claim 1, wherein R₁ is C1-C3 alkyl.

5. The compound or salt of claim 1, wherein R₁' is C1-C3 alkyl, halo C1-C6 alkyl, cyano C1-C6 alkyl, nitro C1-C6 alkyl, or benzyl.

6. The compound or salt of claim 1, wherein the fluorophore moiety is a moiety of an Alexa Fluor dye, a fluorescein dye, or a cyanine dye.

7. The compound or salt of claim 1, wherein m is 4-6.

8. The compound or salt of claim 7, wherein m is 6.

9. The compound or salt of claim 1, wherein n is 1-3.

10. The compound or salt of claim 9, wherein n is 3.

11. The compound or salt of claim 1, which is: